(12) United States Patent
Babkes et al.

(10) Patent No.: US 9,463,107 B2
(45) Date of Patent: Oct. 11, 2016

(54) VARIABLE SIZE INTRAGASTRIC IMPLANT DEVICES

(75) Inventors: Mitchell H. Babkes, Santa Clarita, CA (US); Sean Snow, Carpinteria, CA (US)

(73) Assignee: Apollo Endosurgery, Inc., Austin, TX (US)

( * ) Notice: Subject to any disclaimer, the term of this patent is extended or adjusted under 35 U.S.C. 154(b) by 156 days.

(21) Appl. No.: 13/272,106

(22) Filed: Oct. 12, 2011

(65) Prior Publication Data

US 2012/0095492 A1 Apr. 19, 2012

Related U.S. Application Data

(60) Provisional application No. 61/394,145, filed on Oct. 18, 2010, provisional application No. 61/394,592, filed on Oct. 19, 2010, provisional application No. 61/394,685, filed on Oct. 19, 2010.

(51) Int. Cl.
*A61F 2/04* (2013.01)
*A61F 5/00* (2006.01)

(52) U.S. Cl.
CPC .............. *A61F 5/004* (2013.01); *A61F 5/003* (2013.01)

(58) Field of Classification Search
CPC ............................. A61F 5/0003; A61B 17/02
USPC ................................................. 606/191, 198
See application file for complete search history.

(56) References Cited

U.S. PATENT DOCUMENTS

| 1,702,974 | A | 2/1929 | MacDonald |
| 2,087,604 | A | 7/1937 | Mosher |
| 2,163,048 | A | 6/1939 | McKee |
| 2,619,138 | A | 11/1952 | Marler |
| 3,667,081 | A | 6/1972 | Burger |

(Continued)

FOREIGN PATENT DOCUMENTS

| CN | 1250382 A | 4/2000 |
| CN | 1367670 A | 9/2002 |

(Continued)

OTHER PUBLICATIONS

Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

(Continued)

*Primary Examiner* — Richard Louis
(74) *Attorney, Agent, or Firm* — Gordon & Jacobson, P.C.

(57) ABSTRACT

Transoral obesity treatment devices and related methods for operation thereof are described which occupy space within a stomach and/or stimulate the stomach wall. The transoral obesity treatment devices and related methods are intended to assist a patient in maintaining a healthy body weight. Features of the devices include insertion transorally and without invasive surgery, without associated patient risks of invasive surgery, and without substantial patient discomfort. The life span of these devices may be material-dependent upon long-term survivability within an acidic stomach, but is intended to last one year or longer. The devices have the capacity to vary in size and are desirably self-actuating in that they change shape and/or volume using internal motors or actuators. The changing character of the devices helps prevent the person's stomach from compensating for the implant, such as sometimes happens with static intragastric devices.

21 Claims, 10 Drawing Sheets

(56) References Cited

U.S. PATENT DOCUMENTS

| | | |
|---|---|---|
| 3,719,973 A | 3/1973 | Bell |
| 3,840,018 A | 10/1974 | Heifetz |
| 3,919,724 A | 11/1975 | Sanders |
| 4,118,805 A | 10/1978 | Reimels |
| 4,364,379 A | 12/1982 | Finney |
| 4,416,267 A | 11/1983 | Garren et al. |
| 4,430,392 A | 2/1984 | Kelley |
| 4,485,805 A | 12/1984 | Foster |
| 4,545,367 A | 10/1985 | Tucci |
| 4,586,501 A | 5/1986 | Claracq |
| 4,592,355 A | 6/1986 | Antebi |
| 4,598,699 A | 7/1986 | Garren |
| 4,607,618 A | 8/1986 | Angelchik |
| 4,636,213 A | 1/1987 | Pakiam |
| 4,648,383 A | 3/1987 | Angelchik |
| 4,694,827 A | 9/1987 | Weiner |
| 4,723,547 A | 2/1988 | Kullas |
| 4,739,758 A | 4/1988 | Lai et al. |
| 4,773,432 A | 9/1988 | Rydell |
| 4,774,956 A | 10/1988 | Kruse et al. |
| 4,844,068 A | 7/1989 | Arata et al. |
| 4,881,939 A | 11/1989 | Newman |
| 4,899,747 A | 2/1990 | Garren et al. |
| 4,925,446 A | 5/1990 | Garay et al. |
| 4,930,535 A | 6/1990 | Rinehold |
| 4,950,258 A | 8/1990 | Kawai |
| 4,969,899 A | 11/1990 | Cox |
| 5,074,868 A | 12/1991 | Kuzmak |
| 5,084,061 A | 1/1992 | Gau |
| 5,211,371 A | 5/1993 | Coffee |
| 5,226,429 A | 7/1993 | Kuzmak |
| 5,255,690 A | 10/1993 | Keith |
| 5,259,399 A | 11/1993 | Brown |
| 5,289,817 A | 3/1994 | Williams |
| 5,308,324 A | 5/1994 | Hammerslag |
| 5,312,343 A | 5/1994 | Krog et al. |
| 5,449,368 A | 9/1995 | Kuzmak |
| 5,514,176 A | 5/1996 | Bosley |
| 5,527,340 A | 6/1996 | Vogel |
| 5,540,701 A | 7/1996 | Sharkey |
| 5,547,458 A * | 8/1996 | Ortiz et al. ............ 600/204 |
| 5,601,604 A | 2/1997 | Vincent |
| 5,658,298 A | 8/1997 | Vincent |
| 5,693,014 A | 12/1997 | Abele |
| 5,725,507 A | 3/1998 | Petrick |
| 5,748,200 A | 5/1998 | Funahashi |
| 5,776,160 A | 7/1998 | Pasricha |
| 5,819,749 A | 10/1998 | Lee |
| 5,820,584 A | 10/1998 | Crabb |
| RE36,176 E | 3/1999 | Kuzmak |
| 5,938,669 A | 8/1999 | Klaiber |
| 6,074,341 A | 6/2000 | Anderson |
| 6,102,678 A | 8/2000 | Peclat |
| 6,102,897 A | 8/2000 | Lang |
| 6,102,922 A | 8/2000 | Jakobsson |
| 6,152,922 A | 11/2000 | Ouchi |
| 6,183,492 B1 * | 2/2001 | Hart et al. ............ 606/194 |
| 6,264,700 B1 | 7/2001 | Kilcoyne et al. |
| 6,290,575 B1 | 9/2001 | Shipp |
| 6,322,538 B1 | 11/2001 | Elbert et al. |
| 6,450,946 B1 * | 9/2002 | Forsell ............ 600/37 |
| 6,454,699 B1 | 9/2002 | Forsell |
| 6,454,785 B2 | 9/2002 | De Hoyos Garza |
| 6,464,628 B1 | 10/2002 | Forsell |
| 6,470,892 B1 | 10/2002 | Forsell |
| 6,503,264 B1 | 1/2003 | Birk |
| 6,511,490 B2 | 1/2003 | Robert |
| 6,540,789 B1 | 4/2003 | Silverman et al. |
| 6,547,801 B1 | 4/2003 | Dargent |
| 6,579,301 B1 | 6/2003 | Bales et al. |
| 6,629,776 B2 | 10/2003 | Bell |
| 6,675,809 B2 | 1/2004 | Stack et al. |
| 6,682,473 B1 | 1/2004 | Matsuura |
| 6,733,512 B2 | 5/2004 | McGhan |
| 6,733,513 B2 | 5/2004 | Boyle |
| 6,746,460 B2 | 6/2004 | Gannoe |
| 6,776,783 B1 | 8/2004 | Frantzen |
| 6,840,257 B2 | 1/2005 | Dario |
| 6,845,776 B2 | 1/2005 | Stack et al. |
| 6,905,471 B2 * | 6/2005 | Leivseth et al. ............ 600/591 |
| 6,960,233 B1 | 11/2005 | Berg |
| 6,981,978 B2 | 1/2006 | Gannoe |
| 6,981,980 B2 | 1/2006 | Sampson et al. |
| 6,994,095 B2 | 2/2006 | Burnett |
| 7,008,419 B2 | 3/2006 | Shadduck |
| 7,020,531 B1 | 3/2006 | Colliou |
| 7,033,384 B2 | 4/2006 | Gannoe et al. |
| 7,037,344 B2 | 5/2006 | Kagan et al. |
| 7,056,305 B2 | 6/2006 | Garza Alvarez |
| 7,090,699 B2 | 8/2006 | Geitz |
| 7,214,233 B2 | 5/2007 | Gannoe et al. |
| 7,220,237 B2 | 5/2007 | Gannoe et al. |
| 7,220,284 B2 | 5/2007 | Kagan et al. |
| 7,223,277 B2 | 5/2007 | DeLegge |
| 7,320,696 B2 | 1/2008 | Gazi et al. |
| 7,347,875 B2 | 3/2008 | Levine et al. |
| 7,354,454 B2 | 4/2008 | Stack et al. |
| 7,476,256 B2 | 1/2009 | Meade et al. |
| 7,510,559 B2 | 3/2009 | Deem et al. |
| 7,608,114 B2 | 10/2009 | Levine et al. |
| 7,628,442 B1 | 12/2009 | Spencer |
| 7,682,330 B2 | 3/2010 | Meade et al. |
| 7,695,446 B2 | 4/2010 | Levine et al. |
| 7,699,863 B2 | 4/2010 | Marco et al. |
| 7,753,870 B2 | 7/2010 | Demarais et al. |
| 7,771,382 B2 | 8/2010 | Levine et al. |
| 7,794,447 B2 | 9/2010 | Dann et al. |
| 7,815,589 B2 | 10/2010 | Meade et al. |
| 7,837,643 B2 | 11/2010 | Levine et al. |
| 7,841,503 B2 | 11/2010 | Sonnenschein et al. |
| 7,883,525 B2 | 2/2011 | DeLegge |
| 7,931,693 B2 | 4/2011 | Binmoeller |
| 7,981,162 B2 | 7/2011 | Stack et al. |
| 8,029,455 B2 | 10/2011 | Stack et al. |
| 8,032,223 B2 | 10/2011 | Imran |
| 8,075,582 B2 | 12/2011 | Lointier |
| 8,162,969 B2 | 4/2012 | Brister |
| 8,187,297 B2 | 5/2012 | Makower |
| 8,216,266 B2 | 7/2012 | Hively |
| 2002/0019577 A1 * | 2/2002 | Arabia et al. ............ 600/16 |
| 2002/0055757 A1 | 5/2002 | Torre |
| 2002/0095181 A1 | 7/2002 | Beyar |
| 2002/0139208 A1 | 10/2002 | Yatskov |
| 2002/0183782 A1 | 12/2002 | Tsugita |
| 2003/0045896 A1 | 3/2003 | Murphy |
| 2003/0073880 A1 | 4/2003 | Polsky |
| 2003/0074054 A1 | 4/2003 | Duerig |
| 2003/0078611 A1 * | 4/2003 | Hashiba et al. ............ 606/191 |
| 2003/0100822 A1 * | 5/2003 | Lew et al. ............ 600/365 |
| 2003/0106761 A1 | 6/2003 | Taylor |
| 2003/0109935 A1 | 6/2003 | Geitz |
| 2003/0144575 A1 * | 7/2003 | Forsell ............ 600/29 |
| 2003/0153905 A1 | 8/2003 | Edwards et al. |
| 2003/0158570 A1 | 8/2003 | Ferrazzi |
| 2004/0044357 A1 | 3/2004 | Gannoe et al. |
| 2004/0092892 A1 | 5/2004 | Kagan et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0143342 A1 | 7/2004 | Stack |
| 2004/0148034 A1 | 7/2004 | Kagan |
| 2004/0172142 A1 | 9/2004 | Stack |
| 2004/0186503 A1 | 9/2004 | DeLegge |
| 2005/0033332 A1 | 2/2005 | Burnett |
| 2005/0049718 A1 | 3/2005 | Dann et al. |
| 2005/0055039 A1 | 3/2005 | Burnett et al. |
| 2005/0085923 A1 | 4/2005 | Levine et al. |
| 2005/0096692 A1 | 5/2005 | Linder et al. |
| 2005/0110280 A1 | 5/2005 | Guy |
| 2005/0131485 A1 | 6/2005 | Knudson |
| 2005/0190070 A1 | 9/2005 | Rudduck |
| 2005/0192614 A1 | 9/2005 | Binmoeller |
| 2005/0192615 A1 | 9/2005 | Torre |
| 2005/0197714 A1 | 9/2005 | Sayet |

(56) References Cited

U.S. PATENT DOCUMENTS

| | | | |
|---|---|---|---|
| 2005/0228504 A1* | 10/2005 | Demarais | 623/23.65 |
| 2005/0240279 A1 | 10/2005 | Kagan | |
| 2005/0250979 A1 | 11/2005 | Coe | |
| 2005/0256533 A1 | 11/2005 | Roth | |
| 2005/0261711 A1 | 11/2005 | Okada | |
| 2005/0267595 A1 | 12/2005 | Chen et al. | |
| 2005/0267596 A1 | 12/2005 | Chen et al. | |
| 2005/0273060 A1 | 12/2005 | Levy et al. | |
| 2005/0277975 A1 | 12/2005 | Saadat | |
| 2006/0020278 A1 | 1/2006 | Burnett | |
| 2006/0025799 A1 | 2/2006 | Basu | |
| 2006/0069403 A1 | 3/2006 | Shalon | |
| 2006/0106288 A1 | 5/2006 | Roth | |
| 2006/0142700 A1 | 6/2006 | Sobelman | |
| 2006/0178691 A1 | 8/2006 | Binmoeller | |
| 2006/0190019 A1 | 8/2006 | Gannoe | |
| 2006/0217762 A1* | 9/2006 | Maahs et al. | 606/213 |
| 2006/0229702 A1 | 10/2006 | Agnew | |
| 2006/0252983 A1 | 11/2006 | Lembo et al. | |
| 2007/0010864 A1 | 1/2007 | Dann et al. | |
| 2007/0016262 A1 | 1/2007 | Gross et al. | |
| 2007/0021761 A1 | 1/2007 | Phillips | |
| 2007/0078476 A1 | 4/2007 | Hull, Sr. et al. | |
| 2007/0083224 A1 | 4/2007 | Hively | |
| 2007/0100368 A1 | 5/2007 | Quijano et al. | |
| 2007/0118168 A1 | 5/2007 | Lointier et al. | |
| 2007/0135803 A1* | 6/2007 | Belson | 606/1 |
| 2007/0135829 A1 | 6/2007 | Paganon | |
| 2007/0147170 A1 | 6/2007 | Hood | |
| 2007/0149994 A1 | 6/2007 | Sosnowski | |
| 2007/0156013 A1 | 7/2007 | Birk | |
| 2007/0156248 A1 | 7/2007 | Marco | |
| 2007/0173881 A1 | 7/2007 | Birk et al. | |
| 2007/0185374 A1 | 8/2007 | Kick | |
| 2007/0239284 A1 | 10/2007 | Skerven et al. | |
| 2007/0250020 A1 | 10/2007 | Kim | |
| 2007/0265598 A1* | 11/2007 | Karasik | 604/891.1 |
| 2007/0276428 A1 | 11/2007 | Haller | |
| 2007/0288033 A1 | 12/2007 | Murature | |
| 2007/0293716 A1 | 12/2007 | Baker et al. | |
| 2008/0015618 A1 | 1/2008 | Sonnenschein et al. | |
| 2008/0058840 A1 | 3/2008 | Albrecht et al. | |
| 2008/0058887 A1 | 3/2008 | Griffin et al. | |
| 2008/0065122 A1 | 3/2008 | Stack | |
| 2008/0071305 A1 | 3/2008 | DeLegge | |
| 2008/0097513 A1 | 4/2008 | Kaji et al. | |
| 2008/0167606 A1 | 7/2008 | Dann | |
| 2008/0172079 A1 | 7/2008 | Birk | |
| 2008/0208240 A1 | 8/2008 | Paz | |
| 2008/0208241 A1 | 8/2008 | Weiner et al. | |
| 2008/0221595 A1 | 9/2008 | Surti | |
| 2008/0228205 A1 | 9/2008 | Sharkey | |
| 2008/0234718 A1 | 9/2008 | Paganon et al. | |
| 2008/0234834 A1 | 9/2008 | Meade et al. | |
| 2008/0243071 A1 | 10/2008 | Quijano | |
| 2008/0243166 A1 | 10/2008 | Paganon et al. | |
| 2008/0249635 A1 | 10/2008 | Weitzner et al. | |
| 2008/0255601 A1 | 10/2008 | Birk | |
| 2008/0255678 A1 | 10/2008 | Cully et al. | |
| 2008/0262529 A1 | 10/2008 | Jacques | |
| 2008/0306506 A1 | 12/2008 | Leatherman | |
| 2009/0012553 A1 | 1/2009 | Swain et al. | |
| 2009/0082644 A1* | 3/2009 | Li | 600/302 |
| 2009/0093767 A1 | 4/2009 | Kelleher | |
| 2009/0093837 A1 | 4/2009 | Dillon | |
| 2009/0131968 A1 | 5/2009 | Birk | |
| 2009/0132031 A1 | 5/2009 | Cook | |
| 2009/0149879 A1* | 6/2009 | Dillon | 606/192 |
| 2009/0177215 A1 | 7/2009 | Stack | |
| 2009/0198210 A1 | 8/2009 | Burnett et al. | |
| 2009/0216337 A1 | 8/2009 | Egan | |
| 2009/0259246 A1 | 10/2009 | Eskaros et al. | |
| 2009/0275973 A1 | 11/2009 | Chen et al. | |
| 2009/0287231 A1 | 11/2009 | Brooks et al. | |
| 2009/0299327 A1 | 12/2009 | Tilson | |
| 2009/0299486 A1 | 12/2009 | Shohat et al. | |
| 2009/0312597 A1 | 12/2009 | Bar et al. | |
| 2010/0030017 A1 | 2/2010 | Baker et al. | |
| 2010/0049224 A1* | 2/2010 | Vargas | 606/153 |
| 2010/0081991 A1 | 4/2010 | Swisher | |
| 2010/0082047 A1 | 4/2010 | Cosgrove | |
| 2010/0087843 A1 | 4/2010 | Bertolote | |
| 2010/0100079 A1 | 4/2010 | Berkcan | |
| 2010/0100115 A1 | 4/2010 | Soetermans et al. | |
| 2010/0121371 A1 | 5/2010 | Brooks et al. | |
| 2010/0168782 A1 | 7/2010 | Hancock | |
| 2010/0168783 A1 | 7/2010 | Murature | |
| 2010/0174307 A1 | 7/2010 | Birk | |
| 2010/0198249 A1 | 8/2010 | Sabliere | |
| 2010/0234937 A1 | 9/2010 | Wang | |
| 2010/0249822 A1 | 9/2010 | Nihalani | |
| 2010/0249825 A1* | 9/2010 | Nihalani | 606/198 |
| 2010/0256775 A1 | 10/2010 | Belhe et al. | |
| 2010/0256776 A1 | 10/2010 | Levine et al. | |
| 2010/0261390 A1 | 10/2010 | Gardner | |
| 2010/0274194 A1 | 10/2010 | Sobelman | |
| 2010/0286628 A1 | 11/2010 | Gross | |
| 2010/0305590 A1 | 12/2010 | Holmes et al. | |
| 2010/0331756 A1 | 12/2010 | Meade et al. | |
| 2010/0332000 A1 | 12/2010 | Forsell | |
| 2011/0009897 A1 | 1/2011 | Forsell | |
| 2011/0106113 A1* | 5/2011 | Tavakkolizadeh et al. | 606/151 |
| 2011/0307075 A1 | 12/2011 | Sharma | |
| 2012/0022561 A1 | 1/2012 | Forsell | |
| 2012/0095483 A1 | 4/2012 | Babkes | |
| 2012/0221037 A1 | 8/2012 | Birk | |

FOREIGN PATENT DOCUMENTS

| | | |
|---|---|---|
| DE | 8804765 U1 | 5/1989 |
| DE | 102007025312 | 11/2008 |
| EP | 1396242 A1 | 3/2004 |
| EP | 1396243 A1 | 3/2004 |
| EP | 1397998 | 3/2004 |
| EP | 1774929 | 4/2007 |
| EP | 2095798 | 9/2009 |
| FR | 2797181 A1 | 2/2001 |
| FR | 2823663 A1 | 10/2002 |
| FR | 2852821 A1 | 10/2004 |
| FR | 2855744 A1 | 12/2004 |
| FR | 2892297 | 4/2007 |
| FR | 2941617 | 8/2010 |
| GB | 2086792 A | 5/1982 |
| JP | S63279854 A | 11/1988 |
| JP | 1049572 A | 2/1989 |
| JP | 63264078 | 10/1998 |
| WO | 8800027 | 1/1988 |
| WO | WO 8800027 | 1/1988 |
| WO | 0015158 A1 | 3/2000 |
| WO | 0032092 | 6/2000 |
| WO | 0110359 A1 | 2/2001 |
| WO | 0149245 A2 | 7/2001 |
| WO | 0166166 A2 | 9/2001 |
| WO | 0235980 A2 | 5/2002 |
| WO | 03055419 A1 | 7/2003 |
| WO | 03105732 A1 | 12/2003 |
| WO | 2004019671 A2 | 3/2004 |
| WO | 2005007231 A1 | 1/2005 |
| WO | 2005094257 | 10/2005 |
| WO | 2005097012 | 10/2005 |
| WO | WO 2005/097012 | 10/2005 |
| WO | 2005110280 | 11/2005 |
| WO | WO 2005/110280 | 11/2005 |
| WO | 2006044640 | 4/2006 |
| WO | 2006020370 | 6/2006 |
| WO | 2006063593 A2 | 6/2006 |
| WO | 2006090018 A1 | 8/2006 |
| WO | WO 2006/111961 | 10/2006 |
| WO | WO 2006/118744 | 11/2006 |
| WO | WO 2007/027812 | 3/2007 |
| WO | WO 2007053556 | 5/2007 |
| WO | 2007076021 | 7/2007 |
| WO | WO 2007/092390 | 8/2007 |
| WO | WO 2007/110866 | 10/2007 |

(56) References Cited

FOREIGN PATENT DOCUMENTS

| WO | 2008101048 | 8/2008 |
|---|---|---|
| WO | WO 2008/112894 | 9/2008 |
| WO | WO 2008/132745 | 11/2008 |
| WO | WO 2010/042062 | 4/2010 |
| WO | 2010074712 | 7/2010 |
| WO | WO 2010/074712 | 7/2010 |
| WO | WO 2010/087757 | 8/2010 |
| WO | WO 2010/117641 | 10/2010 |

OTHER PUBLICATIONS

Baggio et al. 'Biology of Integrins: GLP-1 and GIP'; Gastroenrology; V. 132; pp. 2131-2157; 2007.
Berne et al; 'Physiology'; V. 5; pp. 55-57, 210, 428, 540, 554, 579, 584, 591; 2004.
Boulant et al.; 'Cholecystokinin in Transient Lower Oesophageal Sphincter Relation Due to Gastric Distension in Humans'; Gut; V. 40; pp. 575-581; 1997.
Bradjewin et al; 'Dose Ranging Study of the Effects of Cholecystokinin in Healthy Volunteers'; J. Psychiatr. Neurosci.; V. 16 (2); pp. 91-95; 1991.
Chaudhri; 'Can Gut Hormones Control Appetite and Prevent Obesity?' Diabetes Care; V. 31; Supp 2; pp. S284-S289; Feb. 2008.
Cohen et al.; 'Oxyntomodulin Suppresses Appetite and Reduces Food in Humans'; J. Clin. Endocrinol. Metab.; V. 88; pp. 4696-4701; 2003.
Dakin et al.; 'Oxyntomodulin Inhibits Food Intake in the Rat'; Endocrinology; V. 142; pp. 4244-4250; 2001.
Dakin et al.; 'Peripheral Oxyntomodulin Reduces Food Intake and Body Weight gain in Rats'; Endocrinology; V. 145; No. 6; pp. 2687-2695; Jun. 2004.
Davison; 'Activation of Vagal-Gastric Mechanoreceptors by Cholecystokinin'; Proc. West. Pharmacol. Soc; V. 29; pp. 363-366; 1986.
Ekblad et al.; 'Distribution of Pancreatic Peptide and Peptide-YY'; Peptides; V. 23; pp. 251-261;2002.
Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Houpt; 'Gastrointestinal Factors in Hunger and Satiety'; Neurosci. and Behav. Rev.; V. 6; pp. 145-164; 1982.
Kissileff et al.; 'Peptides that Regulate Food Intake: Cholecystokinin and Stomach Distension Combine to Reduce Food Intake in Humans'; Am. J. Physiol. Regul. Integr. Comp. Physiol.; V. 285; pp. 992-998; 2003.
Naslund et al.; 'Prandial Subcutaneous Injection of Glucagon-Like Peptide'; Br. J. Nutr.; V. 91; pp. 439-446; 2004.
Renshaw et al. 'Peptide YY: A Potential Therapy for Obesity'; Current Drug Targets; V. 6; pp. 171-179; 2005.
Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.
Wynne et al.; 'Subcutaneous Oxyntomodulin Reduces Body Weight in Overweight and Obese Subiects: A Double-Blind Randomized, Controlled Trial': Diabetes; V. 54; pp. 2390-2395; 2005.
BIB Bioenterics Intragastric Balloon Program, 'Take Control of Your Weight and Your Life/The Solution for You,' Inamed Health, pp. 1-2; Jan. 19, 2004.
BIB Bioenterics Intragastric Balloon Program, 'Taking the Next Step/Take Control of Your Weight and Your Life,' Inamed Health, pp. 1-9; Apr. 29, 2004.
BIB Data Sheet Directions for Use, 'BioEnterics Intragastric Balloon System,' Inamed Health, 1-12 pp.
'Living With the Bib/BioEnterics Intragastric Balloon Program,' Inamed Health; 1-10 Patient Information Brochure; pp.; May 1, 2005.

* cited by examiner

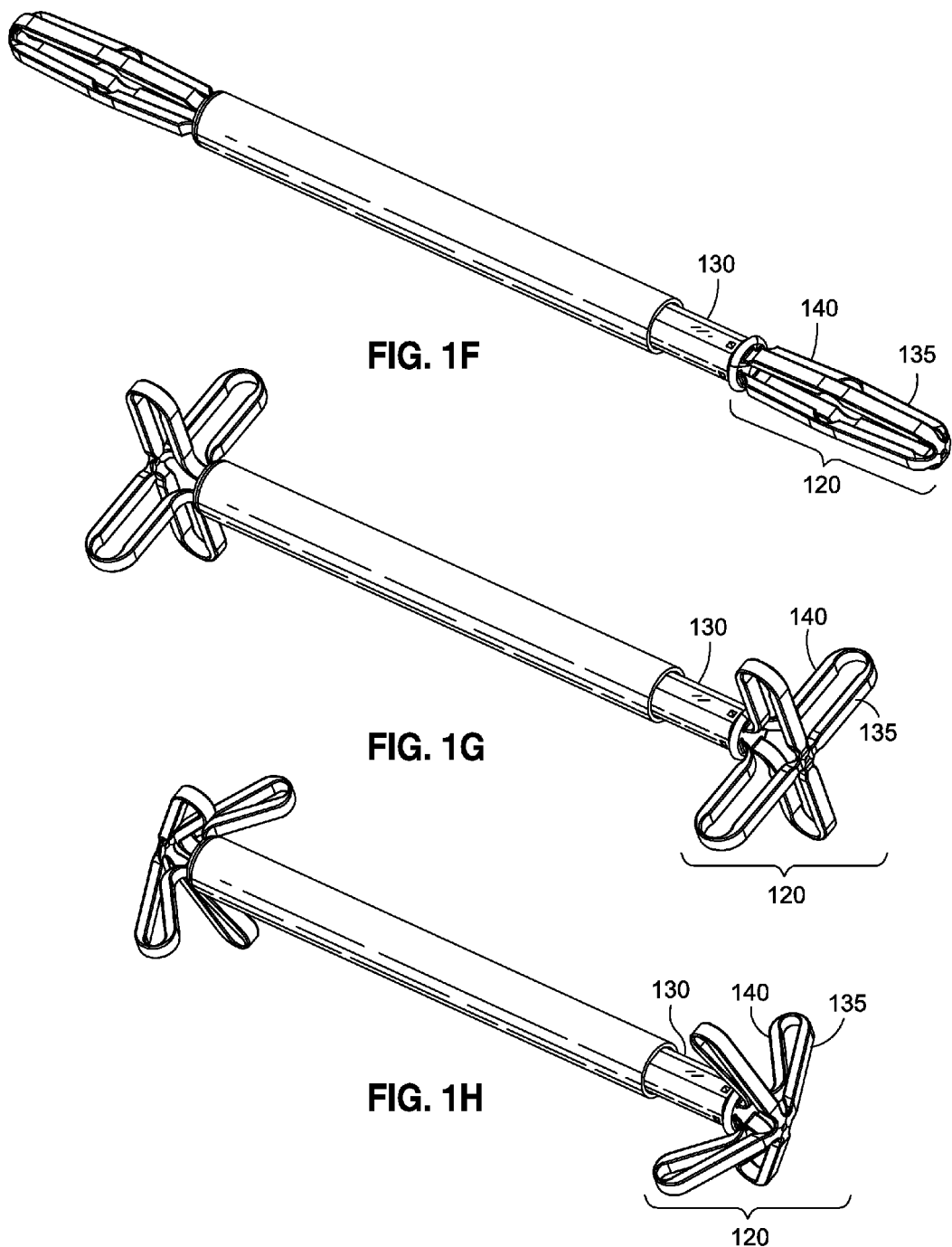

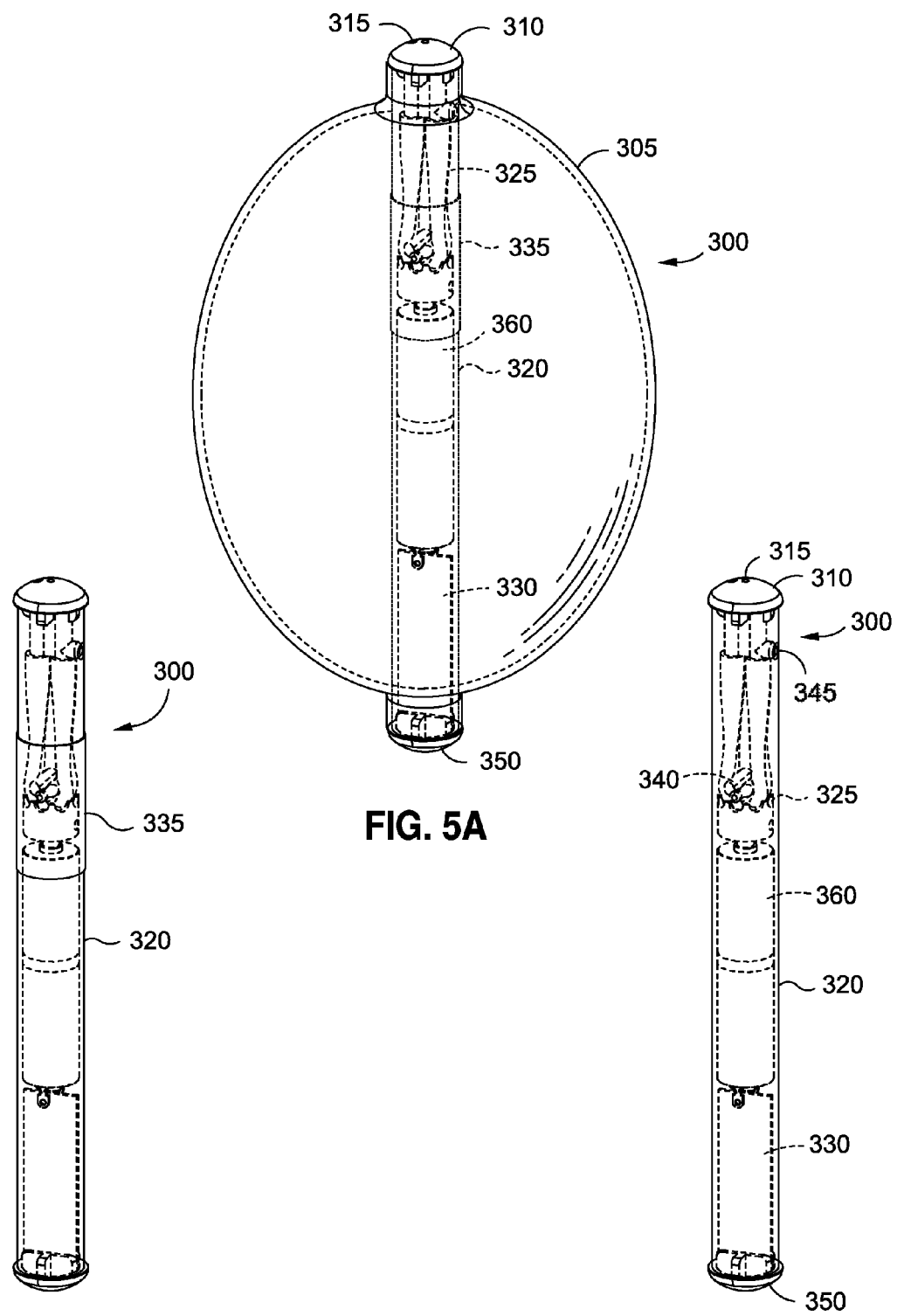

VARIABLE SIZE INTRAGASTRIC IMPLANT DEVICES

RELATED APPLICATIONS

The present application claims priority under 35 U.S.C. §119 to U.S. Provisional Application No. 61/394,145, filed Oct. 18, 2010, U.S. Provisional Application No. 61/394,592, filed Oct. 19, 2010, and U.S. Provisional Application No. 61/394,685, filed Oct. 19, 2010, the disclosures of which are incorporated by reference herein.

FIELD OF THE INVENTION

The present invention generally relates to medical implants and uses thereof for treating obesity and/or obesity-related diseases and, more specifically, to transorally-delivered devices designed to occupy space within a stomach and/or stimulate the stomach wall.

BACKGROUND OF THE INVENTION

Over the last 50 years, obesity has been increasing at an alarming rate and is now recognized by leading government health authorities, such as the Centers for Disease Control (CDC) and National Institutes of Health (NIH), as a disease. In the United States alone, obesity affects more than 60 million individuals and is considered the second leading cause of preventable death. Worldwide, approximately 1.6 billion adults are overweight, and it is estimated that obesity affects at least 400 million adults.

Obesity is caused by a wide range of factors including genetics, metabolic disorders, physical and psychological issues, lifestyle, and poor nutrition. Millions of obese and overweight individuals first turn to diet, fitness and medication to lose weight; however, these efforts alone are often not enough to keep weight at a level that is optimal for good health. Surgery is another increasingly viable alternative for those with a Body Mass Index (BMI) of greater than 40. In fact, the number of bariatric surgeries in the United States is projected to reach approximately 400,000 annually by 2010.

Examples of surgical methods and devices used to treat obesity include the The LAP-BAND® (Allergan, Inc., Irvine, Calif.) gastric band and the LAP-BAND AP® (Allergan, Inc., Irvine, Calif.). However, surgery might not be an option for every obese individual; for certain patients, non-surgical therapies or minimal-surgery options are more effective or appropriate.

For example, intragastric balloons may be utilized as non-surgical or minimal-surgery means for treating obesity. One such inflatable intragastric balloon is described in U.S. Pat. No. 5,084,061 and is commercially available as the BioEnterics Intragastric Balloon System (sold under the BIB® System). These devices are designed to provide therapy for moderately obese individuals who need to shed pounds in preparation for surgery, or as part of a dietary or behavioral modification program.

The BIB® System, for example, comprises a silicone elastomer intragastric balloon that is inserted into the stomach and filled with fluid. Conventionally, the balloons are placed in the stomach in an empty or deflated state and thereafter filled (fully or partially) with a suitable fluid. The balloon occupies space in the stomach, thereby leaving less room available for food and creating a feeling of satiety for the patient. Clinical results with these devices show that for many obese patients, the intragastric balloons significantly help to control appetite and accomplish weight loss.

Placement of such balloons is temporary, and such balloons are typically removed after about six months. One means of removing the balloon is to deflate it by puncturing the balloon, and either aspirating the contents of the balloon or allowing the fluid to pass into the patient's stomach. Alternatively, if the balloon is left in place beyond its designed lifetime, the acids present in a patient's stomach may erode the balloon to the point where it self-deflates. When this occurs, the deflated balloon may pass naturally through the patient's digestive system and be expelled through the bowel. For instance, McGhan, U.S. Pat. No. 6,733,512, describes a self-deflating intragastric balloon that includes a biodegradable inflation valve. After a certain residence time in the stomach, the valve starts to leak and eventually the balloon deflates and passes though the patient's digestive tract.

Despite the advances in the design of intragastric balloons, there remains a need for improved transoral obesity treatment devices.

SUMMARY OF THE INVENTION

Transoral obesity treatment devices generally promote a feeling of satiety in the patient by contacting the insides of the stomach wall, reducing the space in the stomach, or otherwise reducing the amount of food consumed or digested by the patient. The devices have the capacity to vary in size and are desirably self-actuating in that they change shape and/or volume using internal motors or actuators. The changing character of the devices helps prevent the person's stomach from compensating for the implant, such as sometimes happens with static intragastric devices.

In addition, transoral obesity treatment devices generally allow for easy and quick placement and removal. Surgery is usually not required or very minimal. In one aspect, the transoral obesity treatment devices are placed in the patient through the mouth, passing the esophagus and reaching the destination, usually in the stomach region. In most instances, the transoral obesity treatment device does not require suturing or stapling to the esophageal or stomach wall, and remains inside the patient's body for a lengthy period of time (e.g., months or years) before removal.

In one embodiment, the transoral obesity treatment device may be a stomach stimulator, which may fight obesity by stimulating the stomach walls of the patient and occupying space inside the stomach. The stomach stimulator may be an electromechanical device comprising a telescoping body and expandable ends. The ends may be configured to exert a pressure on the inner stomach walls of the patient and, when in the expanded state, prevent the stomach stimulator from entering the patient's intestines. The telescoping body shortens or lengthens the stomach stimulator, either randomly or in accordance with a predefined schedule, such that the patient's body cannot compensate. Studies have shown that obesity may be more effectively reduced when a patient's body cannot compensate to the obesity device.

In one embodiment, a system for treating obesity by applying a pressure to the patient's stomach comprises a central elongated body having an adjustable length. Two collapsible atraumatic feet on opposite ends of the elongated body are each configured to exert pressure on the patient's stomach when in a deployed position. An actuator within the central elongated body adjusts the length of the body and simultaneously the distance between the atraumatic feet. The two collapsible atraumatic feet may comprise balloon-like structures, or they may comprise an array of living hinges that may be unfolded to an elongated delivery configuration and folded outward to a deployed configuration. In the latter configuration, the array of living hinges are in an X-shape. The actuator may comprise an electronic motor, and further may include a control circuit board having a battery and a memory. The actuator control circuit board further may have a transceiver, and the system further includes a remote control for instructing the motor from outside the patient's body. In one embodiment, the actuator comprises a telescoping screw driven by the motor. Alternatively, the actuator comprises a polymer element that is acid-activated to lengthen in a highly acidic environment, and the central elongated body includes through holes for exposing the polymer element to the stomach environment. The central elongated body may comprise a series of telescoping tubular members having apertures along their lengths. In one embodiment, the atraumatic feet include uneven external surface stimulation features.

In the system having the elastic balloon, an aseptic ring may be provided that fits around a portion of the exterior of the body and contact the stomach liquid when the stomach liquid is inside the elastic balloon. The device further may include a control circuit board having a battery and a memory. The control circuit board may also have a transceiver, and the system further includes a remote control for instructing the motor from outside the patient's body. In one embodiment, the elastic balloon includes uneven external surface stimulation features. In another embodiment, the elastic balloon is shaped to encourage rotation within the stomach, such as by being formed in an aggregation of spheres, or having a plurality of outwardly projecting legs terminating in rounded or bulbous feet.

In yet another embodiment, the transoral obesity treatment device may be a variable size balloon device. The device may include a peristaltic pump for inflating or deflating the balloon. Instead of saline, the pump may fill the balloon with naturally-existing stomach fluid already present in the patient's stomach. The pump may be controlled by a motor sealed off from the acidic stomach fluid. The device may further include an aseptic ring inside the balloon intended to disinfect the stomach fluids retained inside the balloon. In one aspect, the motor may be controlled by an electronic device outside the patient's body.

Another system disclosed herein for preventing obesity by occupying space inside the patient's stomach comprises an elastic balloon configured to be variably filled with stomach liquid. A body of the implantable device attached to the elastic balloon is configured to inflate and deflate the elastic balloon by transferring stomach liquid into and out of the elastic balloon. A peristaltic pumping device housed within the body of the implantable device transfers the stomach liquid from outside the elastic balloon to inside the elastic balloon in a first mode of operation, and further transfers the stomach liquid from inside the elastic balloon to outside the elastic balloon in a second mode of operation. The body of the implantable device further may house a motor configured to operate the peristaltic pumping device. The motor rotates rollers that are in contact with a pair of flexible tubes that form a conduit between an external opening located outside the elastic balloon and an internal opening located within the inner cavity of the elastic balloon.

BRIEF DESCRIPTION OF THE DRAWINGS

The following detailed descriptions are given by way of example, but not intended to limit the scope of the disclosure solely to the specific embodiments described herein, may best be understood in conjunction with the accompanying drawings in which:

FIG. 1F illustrates a close up view of an end portion of a stomach stimulator in a folded state.

FIG. 1G illustrates a close up view of an end portion of a stomach stimulator in a deployed or unfolded state.

FIG. 1H illustrates a close up view of an end portion of a stomach stimulator in a pressuring state.

FIG. 5A illustrates a perspective view of a balloon device with the balloon inflated.

FIG. 5B illustrates a balloon device with a silver band.

FIG. 5C illustrates a perspective view of a balloon device without the outer balloon shell.

DESCRIPTION OF THE DETAILED EMBODIMENTS

Figure 1A:
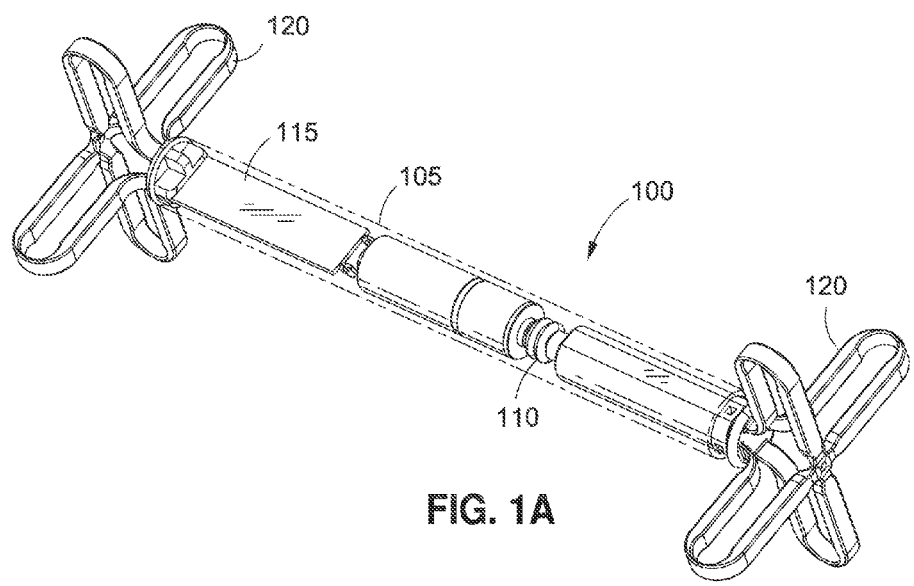
FIG. 1A illustrates a perspective view of an elongated stomach stimulator having soft, folded feet and a variable length.

Persons skilled in the art will readily appreciate that various aspects of the disclosure may be realized by any number of methods and devices configured to perform the intended functions. Stated differently, other methods and devices may be incorporated herein to perform the intended functions. It should also be noted that the drawing Figures referred to herein are not all drawn to scale, but may be exaggerated to illustrate various aspects of the invention, and in that regard, the drawing Figures should not be construed as limiting. Finally, although the present disclosure may be described in connection with various medical principles and beliefs, the present disclosure should not be bound by theory.

By way of example, the present disclosure will reference certain transoral obesity treatment devices. Nevertheless, persons skilled in the art will readily appreciate that certain aspects of the present disclosure advantageously may be applied to one of the numerous varieties of transoral obesity treatment devices other than those disclosed herein.

In one aspect, these transoral obesity treatment devices described herein are intended to be placed inside the patient, transorally and without invasive surgery, without associated patient risks of invasive surgery and without substantial patient discomfort. Recovery time may be minimal as no extensive tissue healing is required. The life span of these transoral obesity treatment devices may be material-dependent upon long-term survivability within an acidic stomach, but is intended to last one year or longer.

FIG. 1A illustrates a first embodiment of a variable sized transoral obesity treatment device, namely a variable-length stomach stimulator 100. The stomach stimulator 100 may include a tubular body 105 (shown in phantom to reveal the inner components), two opposite atraumatic feet 120, a control portion 115, and O-ring seals 110 to prevent stomach juices (e.g., acids) from reaching and corrupting or destroying the control portion 115. The stomach stimulator 100 may reduce appetite as the feet 120 contact and pressure the inside of the patient's stomach walls, thereby affecting nerves and causing early feelings of satiety. In one aspect, the entire stomach stimulator including the feet 120 (in a folded state) may be no larger than 10 millimeters (mm) in diameter, thereby easily passing transorally into the patient's mouth, through the esophagus and into the patient's stomach.

Figure 1B:
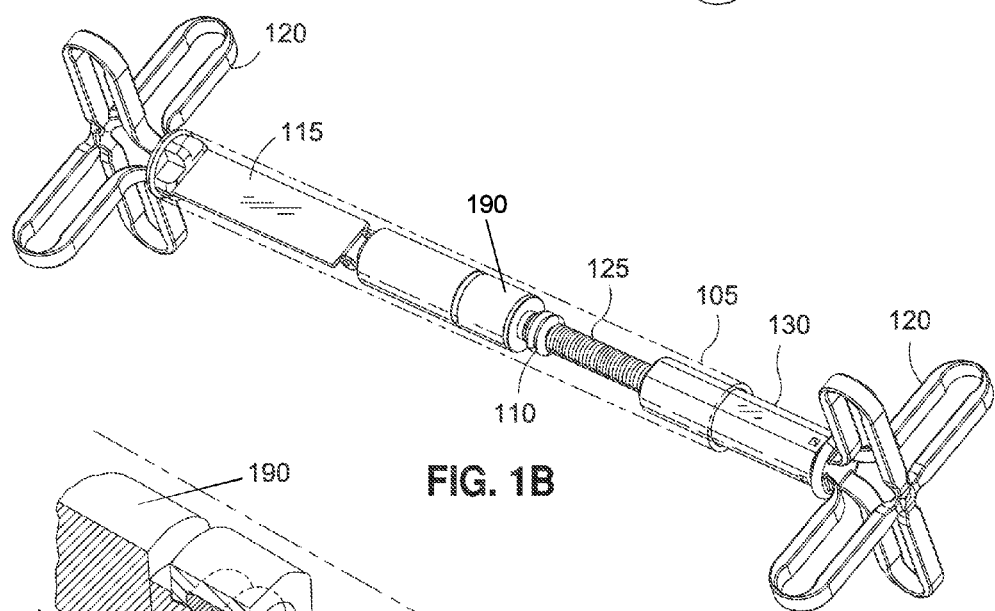
FIG. 1B illustrates a perspective view of the stomach stimulator of FIG. 1A in an extended state.

In one aspect, the stomach stimulator 100 may be configured to telescope to varying lengths. For example, FIG. 1B illustrates the stomach stimulator of FIG. 1A in an extended position. The extension portion 125 may be a screw-like device that telescopically shortens in the direction of the control portion 115 and telescopically lengthens in the direction away from the control portion 115. As shown, the extension portion 125 attaches to a shaft portion 130 such that when the extension portion telescopically lengthens, a part of the intermediate portion extends outside the body 105, thereby "extending" the length of the stomach stimulator 100. The stomach stimulator 100 has the capacity to vary in length and is desirably self-actuating in that the size change occurs from components within. The term, "self-actuating," however, does not exclude a remote connection to an external controller, as will be described below.

Figure 1C:
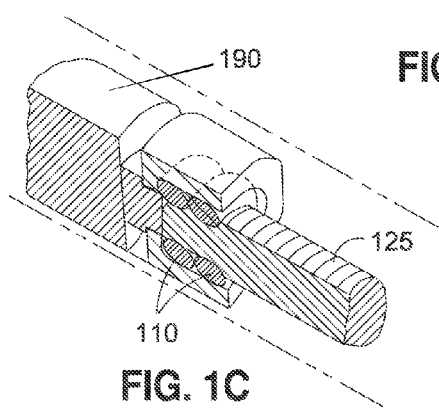
FIG. 1C illustrates a close up view of a portion of the stomach stimulator.

FIG. 1C illustrates a close up view of the extension portion 125 and the dual O-ring seals 110 configured to prevent stomach acid from entering the control portion 115. The control portion 115 may include an implantable motor 190 and gearhead assembly (not shown) configured to drive the extension portion 125. In one aspect, the motor 190 and gearhead assembly may be controlled by an electronic controller also housed in the control portion 115.

Figure 1D:
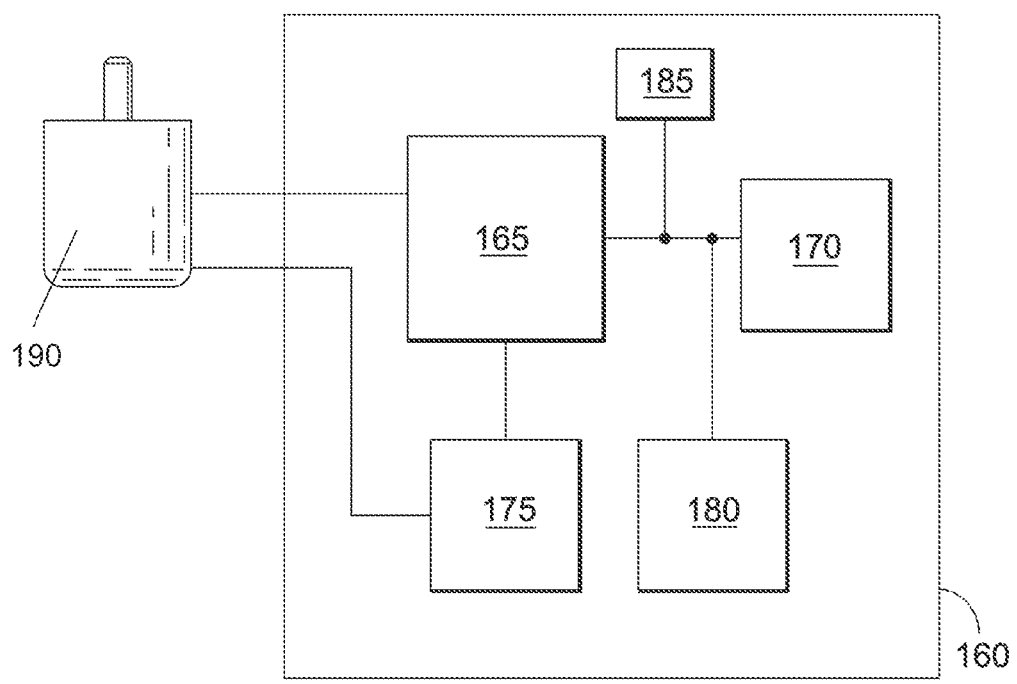
FIG. 1D illustrates a control board for the stomach stimulator.

FIG. 1D illustrates a control board 160 for the stomach stimulator 100 that includes a processor 165, physical memory (e.g., a EEPROM, RAM, ROM, etc.) 170, battery 175 and transceiver 180. The memory may store data such as a schedule for lengthening or shortening the stimulator 100. The transceiver 180 may allow the control board 160 to communicate with an external computer and receive commands and send status information such as current length of the stimulator 100, etc. The control board 160 may further include a sensor 185 configured to detect a current length of the stimulator 100. The control board 160 desirably controls the motor 190 and gearhead assembly (not shown) to drive the telescoping screw 125 (FIG. 1B) to either lengthen or shorten the stimulator 100. In one aspect, the schedule may be updated, changed or interrupted by the transceiver receiving a command from an external computer. In another example, the transceiver may receive a new or updated target stimulator length schedule to assist the stomach stimulator 100 in determining when to adjust the length of the extension portion and the target length to adjust it to. By virtue of the transceiver 180, the stimulator 100 can be controlled externally by hand-held radiofrequency remote controller (not shown). The control board 160 communicates with the remote control unit, and also may contain program information that drives the motor at various random or pre-set distances and at random or preset intervals, causing one end of the stimulator 100 to telescope in and out. The randomness of the telescoping length provides varying pressure, so the patient's body is not likely to compensate, or to adapt to any one typical stomach size.

Figure 1E:
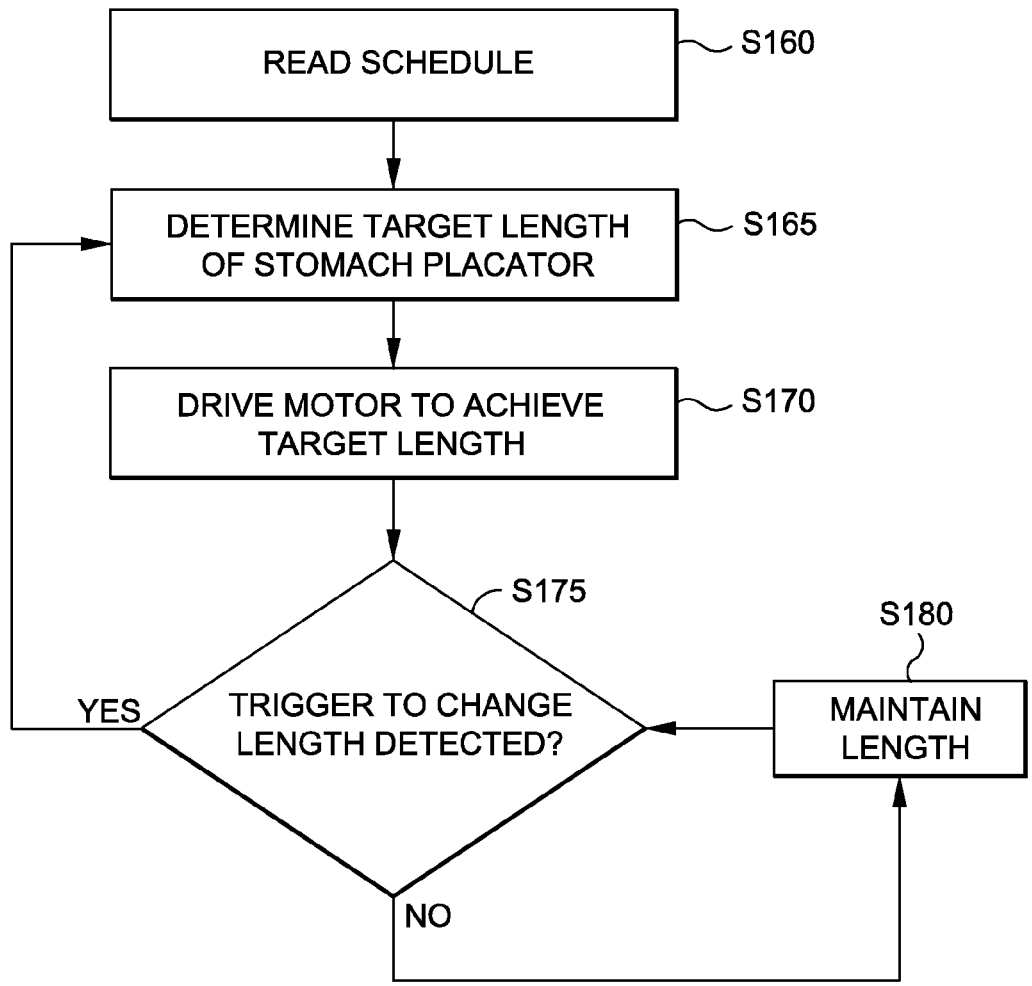
FIG. 1E illustrates a flow chart for controlling the stomach stimulator of FIG. 1A.

FIG. 1E illustrates a flow chart of one example of how the stomach stimulator 100 may function. Initially, when the stomach stimulator 100 is first deployed in the patient's stomach, the stomach stimulator 100 may read a schedule instructing the different lengths that the stimulator may adjust to and at which times at step S160. In one example, the schedule may be a daily schedule that the stomach stimulator 100 follows. Alternatively, the schedule may be for a week, month, year and so forth. After the schedule is read in step S160, the target length may be determined according to the schedule at step S165. At step S170, the motor may be driven to achieve the target length. At step S175, the stomach stimulator 100 may determine if a trigger to change the length is detected. For example, the trigger may be merely determining that the schedule dictates a changing of the length of the stomach stimulator 100. Other triggers may include a command from the external computer to change the length of the stomach stimulator 100. In one aspect, the external computer may issue a "max short" command to have the stomach stimulator 100 shorten itself as much as possible. This command may be advantageous, for instance, when the physician is preparing to remove the stomach stimulator. The stomach stimulator 100 may be configured to override the schedule anytime a command is received from the external computer. In response to the trigger, the stomach stimulator may determine a new target length and drive the motor to achieve the target length. However, if at step S175 no trigger is detected, the stomach stimulator 100 may maintain its current length until a new trigger is detected to alter the length.

In one aspect, changing the length of the stomach stimulator 100 may be advantageous to prevent the patient's body from compensating or adapting to the presence of the stomach stimulator 100. It is thought that if the body is allowed to adapt to the stomach stimulator 100, weight gain due to body compensation may occur decreasing the effectiveness of the stomach stimulator 100. Some clinical indications are that patients adapt to introduction of gastrointestinal implants normally within the first few months of surgery, so early weight gain due to compensation will likely be avoided with the randomly changing stimulator 100. In this sense, by constantly and unpredictably changing the lengths of the stomach stimulator 100, the patient's body cannot adapt effectively, thus promoting weight loss more effectively. In one alternative, the stomach stimulator may be configured to continuously telescope (e.g., never stopping to maintain a particular length). As the stomach muscles churn their contents, the stomach stimulator 100 will essentially randomly shift the point at which pressure is exerted from within the stomach, thus helping to prevent physiological compensation by the stomach for the object within.

In addition, the changing lengths may further have an additional benefit. The pressure exerted by the feet (e.g., feet 120 of FIG. 1A) on the inside of the stomach walls may cause early feelings of satiety. The feet 120 are configured to be atraumatic, in that they are soft and pliable. The feet 120 are desirably formed as an array of fingers of a soft polymer, each preferably having thinned regions so as to function like living hinges. More particularly, each of the spokes of the "X" shaped feet 120 has a rectangular cross-section to facilitate bending in one plane, and thinned regions at three points: where it connects to the stimulator 100, where it connects to the other spokes along an axis of the device, and at a mid-portion which forms the outermost end of each of the spokes in the deployed configuration seen in FIG. 1G. Of course other configurations for the atraumatic feet are contemplated, such as rounded pillows, cups, or the like. The feet 120 also may have a radio-opaque additive molded therein so that they can be seen with X-ray, such as during a removal procedure.

FIG. 1F illustrates the feet 120 in an extended or elongated position to allow easier implantation and removal. However, once implanted inside the patient's stomach, the feet may fold to a deployed state as shown in FIG. 1G. In this state, the feet point outwards and prevent migration through the pylorus, and then the intestines. In one aspect, the length of the inner end portion 135 and outer end portion 140 may be configured to form an "X" pattern that is larger than the opening of the pylorus. FIG. 1H illustrates the feet 120 bending, which may occur when the stomach stimulator 100 is exerting pressure on the stomach walls. Advantageously, even in this pressuring state, the end portion 120 is not able to migrate through the pylorus as the inner portion 140 and the outer portion 135 contact each other and resist the end portion 120 from bending further. In other words, even at the pressuring state, the end 120 is still too large to fit through the pylorus. While shown as three distinct states, the stomach stimulator 100 may be configured to take on any position therebetween.

Figure 2:
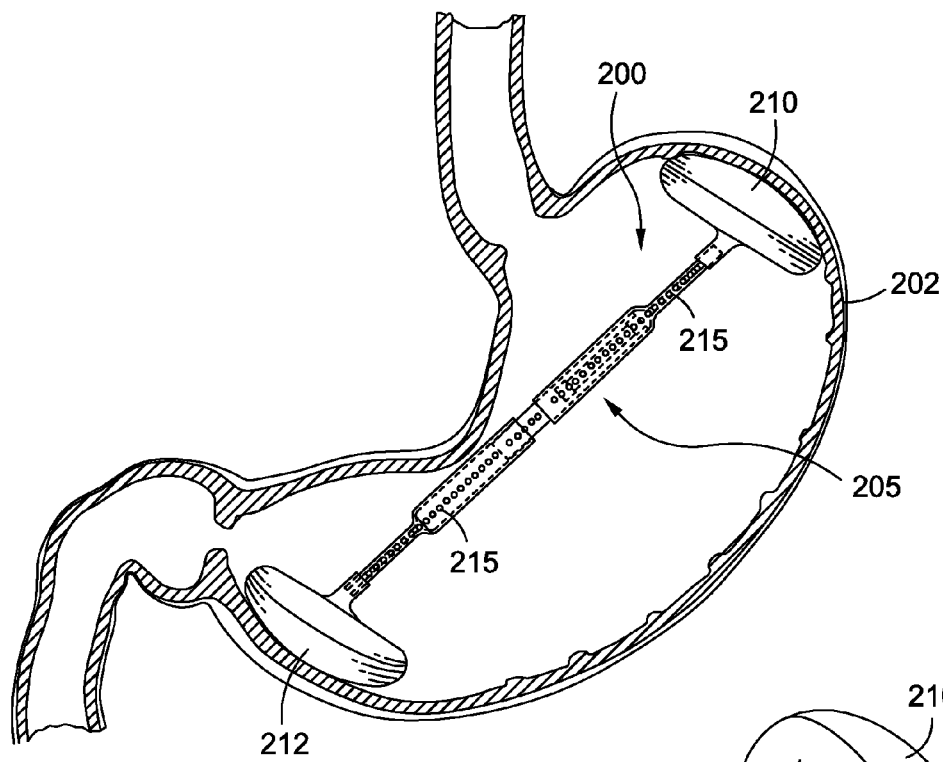
FIG. 2 illustrates a side view of an intragastric obesity treatment device with a piston in a patient's stomach.
Figure 3:
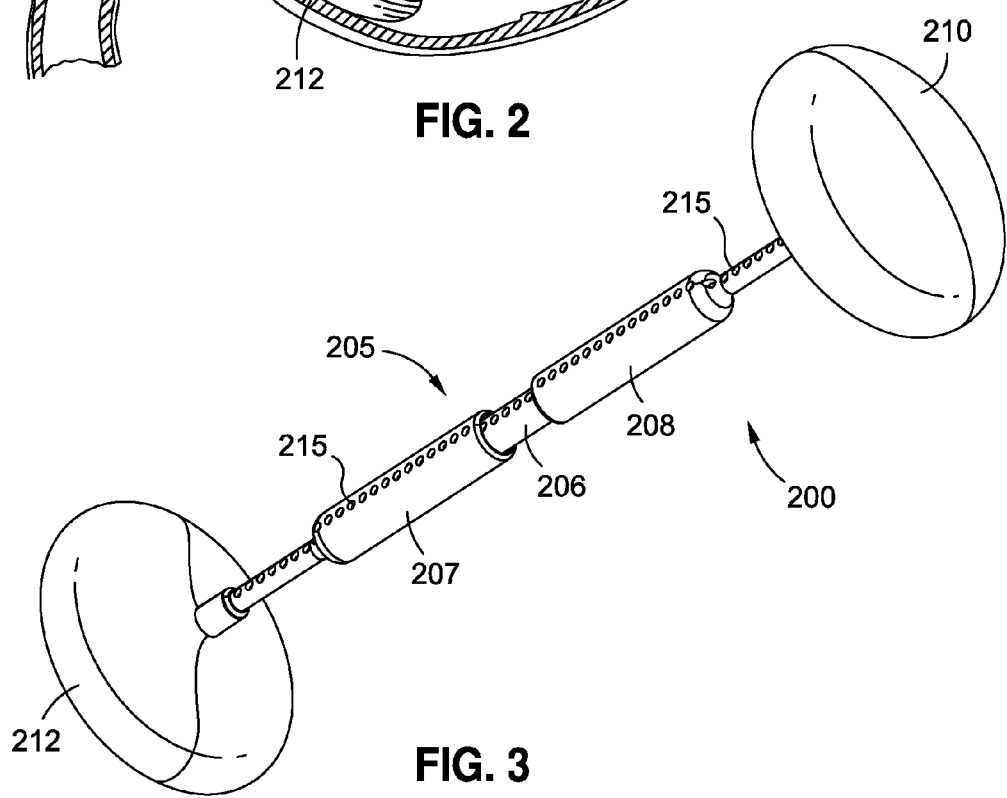
FIG. 3 illustrates a perspective view of an intragastric obesity treatment device with a piston.
Figure 4:
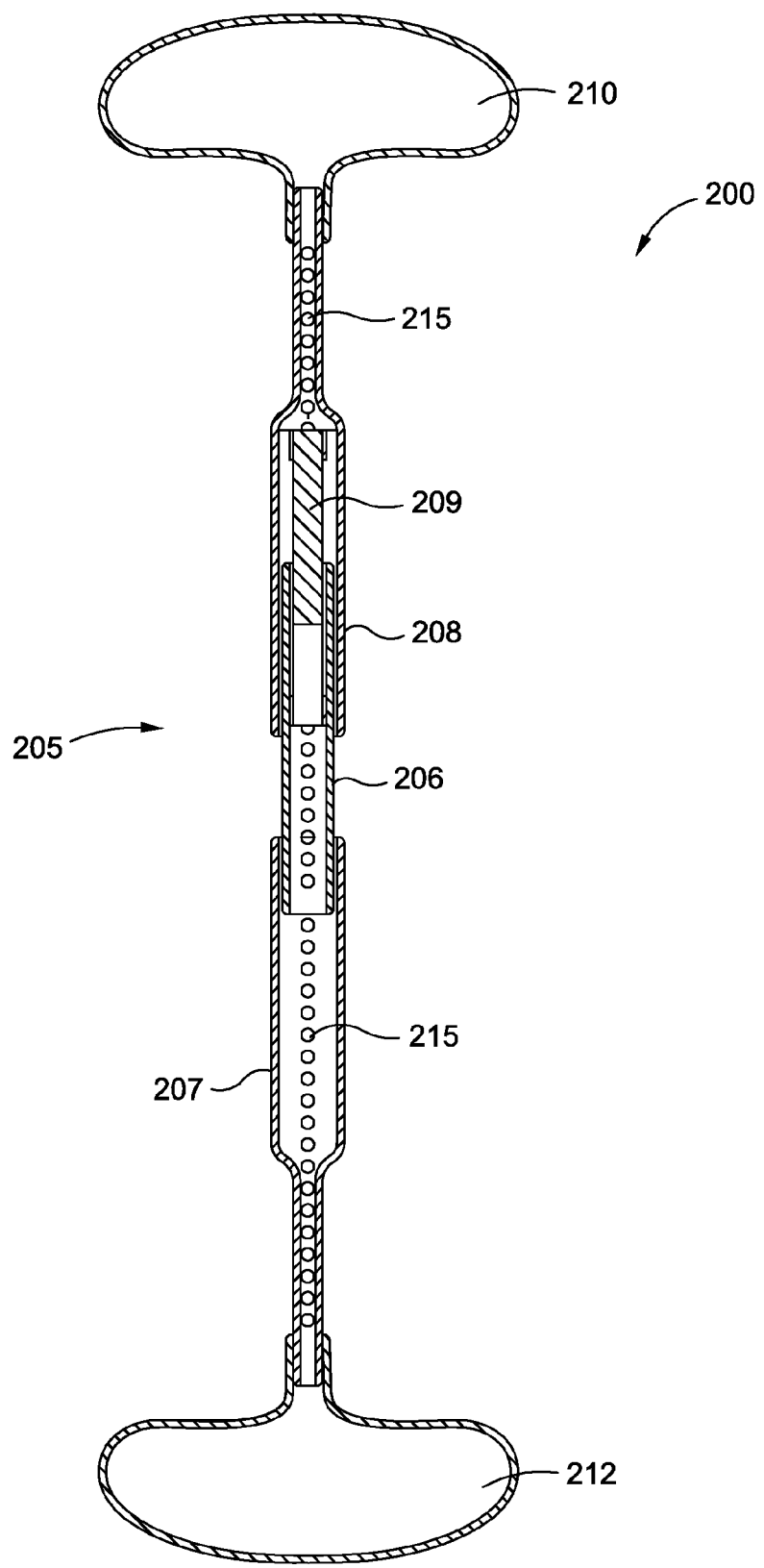
FIG. 4 illustrates a sectional view of an intragastric obesity treatment device with a piston and a motor in accordance with an embodiment of the present invention.

In accordance with another embodiment of the present invention, and with reference to FIGS. 2-4, a gastrointestinal implant, such as an intragastric obesity treatment device 200, may comprise a piston assembly 205, such as a telescoping tube, coupled to two atraumatic, pliable end portions, which are shown in the illustrated monument as balloon feet 210, 212. The piston assembly 205 is configured to bias the balloon feet 210, 212 against the walls of a patient's stomach 202. As the balloon feet 210, 212 exert pressure against the walls of the stomach 202, the patient may experience a feeling of satiety, resulting in a reduced desire to eat, and eventually resulting in weight loss. For example, the balloon 212 may exert pressure on the greater curvature of the stomach, causing the balloon 210 to exert pressure on the cardia. Such cardial pressure may stimulate the release of satiety-inducing hormones, thus reducing meal time food intake. In various embodiments, the shape of the intragastric obesity treatment device 200 appropriately orients the balloon feet 210, 212 within the stomach 202 approximate the greater curvature and the cardia.

As seen in FIG. 3, the piston assembly 205 may comprise a piston 206 disposed within sleeves 207, 208. The piston 206 is fixed with respect to one of the sleeves 207, 208 and was the other toward or away from the first sleeve, causing the balloon feet 210, 212 similarly to move toward or away from each other. In other embodiments, the piston 206 may slide within both sleeves 207, 208.

As seen in the cross-section of FIG. 4, a self-actuating lengthener 209 may be disposed within one of the sleeves 207, 208, for example, within the sleeve 208 (as illustrated in FIG. 4), to facilitate moving the piston 206 within the sleeves 207, 208. Various such devices are contemplated within the scope of the present invention, but, in one embodiment, the self-actuating lengthener 209 may comprise a polymer that is acid-activated. For example, the self-actuating lengthener 209 may comprise a polymer bundle that is capable of expanding up to two times its original length when the polymer bundle is exposed to an acidic environment with a lower pH. Such acid-activated polymers may be referred to as stimuli sensitive polymers, and may comprise polyacrylonitrile (PAN) fibers.

Such polymers are disclosed in the following documents, all of which are hereby incorporated by reference in their entirety: Anasuya Sahoo, et al., "Effect of copolymer architecture on the response of pH sensitive fibers based on acrylonitrile and acrylic acid," *European Polymer Journal* 43 (2007), 1065-1076. Kiyoung Choe and Kwang J. Kim, "Polyacrylonitrile linear actuators: Chemomechanical and electro-chemomechanical properties," *Sensors and Actuators A* 126 (2006), 165-172. R, Samatham, et al., "Electrospun nanoscale polyacrylonitrile artificial muscle," *Smart Materials and Structures* 15 (2006), N152-N156. B. Tondu, et al., "A pH-activated artificial muscle using the McKibben-type braided structure," *Sensors and Actuators A* 150 (2009), 124-130. Ping An Song, et al., "A pH-sensitive Modified Polyacrylamide Hydrogel," *Chinese Chemical Letters*, Vol. 17, No. 3 (2006) 399-402.

Although PAN fibers for acid-activated lengthener are discussed herein, it should be understood that various lengthener are contemplated within the scope of the present invention. For example, all lengthener that are capable of being actuated by substances that may exist in the body, such as stomach juices, enzymes, and/or the like, are within the scope of the present invention. Such substances may be referred to herein as "bodily substances."

Accordingly, as a patient begins to eat, digestive enzymes along with hydrochloric acid (HCL) are secreted into the stomach 202, resulting in a lowered pH in the stomach 202. This lowered pH causes the polymer in the lengthener 209 to expand, which in turn causes the piston assembly 205 to move the balloon feet 210, 212 away from each other to exert pressure on the stomach 202. The pressure stimulates the release of satiety-inducing hormones, reducing meal time food intake. As the patient stops eating and digestion progresses, the pH levels in the stomach 202 begin to rise, resulting in contraction of the polymer in the lengthener 209, which causes the balloon feet 210, 212 to move away from the stomach 202 walls.

With continued reference to FIGS. 2-4, and in accordance with various embodiments, the intragastric obesity treatment device 200 comprises holes 215 to allow stomach juices to come into contact with the lengthener 209 so that it may expand and/or contract. Further, the holes 215 may permit the intragastric obesity treatment device 200 to be properly situated within the stomach 202, such that motion of the stomach juices does not substantially affect the position of the intragastric obesity treatment device 200, other than by causing the lengthener 209 to move the piston assembly 205 and the balloon feet 210, 212. For example, the sleeves 207, 208 and/or the piston 206 may be hollow to allow the stomach juices to flow through the holes 215 and through the sleeves 207, 208 and/or the piston 206 to come into contact with the lengthener 209.

Further, in accordance with various embodiments, the balloon feet 210, 212 may be configured to cushion the ends of the intragastric obesity treatment device 200 as the ends expand against the stomach 202 walls, to reduce the likelihood of ulceration. Although the balloon feet 210, 212 may be referred to as "balloons," this reference is for descriptive purposes only, and not to limit the structures to balloons per se. Rather, the balloon feet 210, 212 are "balloon-like" structures intended to protect the stomach 202 walls, and all such protective structures are contemplated within the scope of the present invention. For example, the balloon feet 210, 212 may comprise compliant structures that expand and contract, such as when the balloon feet 210, 212 are filled after implantation with air, saline, and the like. In other embodiments, the balloon feet 210, 212 may have thicker walls such that they substantially maintain their as-molded shape without inflation. Where the balloon feet 210, 212 maintain their shape, the holes 215 may also be placed in the balloon feet 210, 212 to allow the stomach juices to flow through the balloon feet 210, 212.

The flexible nature of the balloon feet 210, 212 and the small diameter of the rigid piston assembly 205 allows for deployment and/or removal of the intragastric obesity treatment device 200 via a guiding tube placed through a patient's mouth, down the patient's esophagus, and into the patient's stomach 202. The balloon feet 210, 212 are configured to collapse and/or fold down around the piston assembly 205 to allow the intragastric obesity treatment device 200 to be inserted into and/or removed from the stomach 202 via the guiding tube in the esophagus. Alternatively, the intragastric obesity treatment device 200 may be configured to be implanted into or extracted from the stomach 202 without the use of this guiding tube.

Where the balloon feet 210, 212 are inflatable, a fluid tube may be connected to the intragastric obesity treatment device 200 and deployed down the guiding tube through which the device 200 is inserted into or extracted from the stomach. This fluid tube may be coupled to one or both of the balloon feet 210, 212 (in series or in parallel—e.g., one of the balloon feet may be connected to the other balloon via internal tubing in the piston assembly 205) to allow the balloon feet 210, 212 to be filled with air, saline, or other fluid. A syringe may be coupled to the fluid tube outside of the patient's mouth to facilitate filling or draining the balloon feet 210, 212. After implantation/extraction, both of the tubes are removed from the esophagus, resulting in a minimally invasive implantation/extraction procedure.

In another embodiment, where the balloon feet 210, 212 may be self supporting (e.g., thick walls may allow the balloon feet to maintain shape without internal pressure from added air/saline), air may be pre-extracted from the balloon feet 210, 212, creating a partial vacuum to cause the balloon feet 210, 212 to collapse around the piston assembly 205. In this respect, a portion of the piston assembly 205 adjacent each of the balloon feet 210, 212 is relatively thin, permitting collapse of the balloon feet therearound to form a substantially consistent delivery/removal diameter. Then, when the intragastric obesity treatment device 200 is implanted in the stomach, the fluid tube may allow the partial vacuum in the balloon feet 210, 212 to be released, causing them to expand to their self-supported shape.

Regardless of which embodiment of the stomach stimulator 200, the feet 210, 212 may be, for example, an acid-resistant plastic or any other appropriate material injected with radio-opaque additive so that they may be seen with an x-ray machine during the removal procedure. In addition, the tubular body 205 may be constructed, for example, out of a polysulphone, polypropylene or an acid-resistant plastic material configured to resist the strong acidity of the stomach juices.

In another aspect, removal of the stomach stimulator 200 may be easily performed using a standard grabber. Once the ends are folded down and the stomach stimulator 200 is compressed, the entire stomach stimulator 200 may be easily pulled up through the patient's stomach and esophagus and exit the patient's mouth.

FIG. 5A illustrates another embodiment of a transoral obesity treatment device, namely the inflatable balloon device 300. As shown, the inflatable balloon device 300 is inflated and filled with stomach juices naturally occurring and produced in the patient's body. The inflatable balloon device 300 includes an inflatable layer 305 which spans almost the entire length of body 320. In one aspect, the top 310 and bottom 350 of the inflatable balloon device 300 might not be maintained within the inflatable layer 305. At the outer surface of the top 310 is an opening 315. The opening 315 may be configured to allow peristaltic pump 325 to pull stomach juices into the inflatable layer 305 to fill the balloon or to push out stomach juices from inside the inflatable layer 305 to deflate the balloon. The inflatable balloon device 300 may further include an aseptic band 335, a barrier 360 and a control portion 330. By inflating the inflatable balloon device 300 to a volume between 0 milliliters (mL) and 1000 mL (but preferably between 400 mL and 700 mL), the balloon occupies space in the stomach decreasing the amount of space for food, and also stimulates the stomach walls when the inflatable balloon device 300 via inflation and/or migration exerts a pressure on the inner stomach walls. The inflatable balloon device 300 has the capacity to vary in volume and is desirably self-actuating in that the size change occurs from components within. The term, "self-actuating," however, does not exclude a remote connection to an external controller, as will be described below.

FIG. 5B is a deconstructed version of inflatable balloon device 300. In this view, the inflatable layer 305 forming the "balloon" is removed to better illustrate the various other aspects of the inflatable balloon device 300. Here, a portion of the body 320 of the inflatable balloon device 300 is covered by an antiseptic band 335. The band 335 may be a separate piece of metal attached to the body 320, or may be directly integrated into the body 320 as an exterior layer. The band 335 may be constructed of any material with cleansing, antiseptic qualities. In one example, silver may be used to form the band since silver has natural antiseptic qualities. The function of the band 335 is to passively disinfect the stomach fluid inside the inflatable layer 305.

Figure 5D:
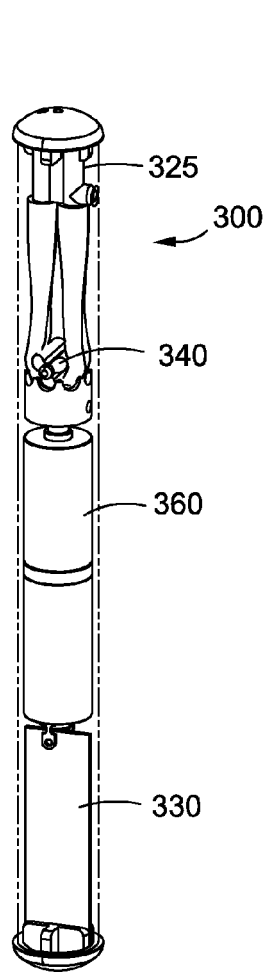
FIG. 5D illustrates a balloon device with the outer body removed.

FIGS. 5C and 5D are further deconstructed versions of the inflatable balloon device of FIG. 5B. Here, the antiseptic band 335 is removed to better show the portion of the tubular body 320 otherwise blocked from view by the band 335. As shown, the body 320 may house a number of components. For example, the body may contain a peristaltic pump 325, rollers 340 operating in conjunction with the pump 325, a barrier portion 360 and a control portion 330. The tubular body 320 may be attached to a top 310 and bottom 340. The tubular body 320 may include a hole 345, and the top 310 may also include a hole 315. The first hole is located at the top 315 and the second hole 355 is located on the side of the body 345. The stomach fluid is pumped into and out of the inflatable balloon device 300 via these two holes since one of the holes (e.g., hole 345) is located inside the inflatable layer 305 and the other hole (e.g., hole 315) is located outside the inflatable layer 305. In FIG. 5D the tubular body 320 is removed to better show the peristaltic pump and the control board 330.

Figure 5E:
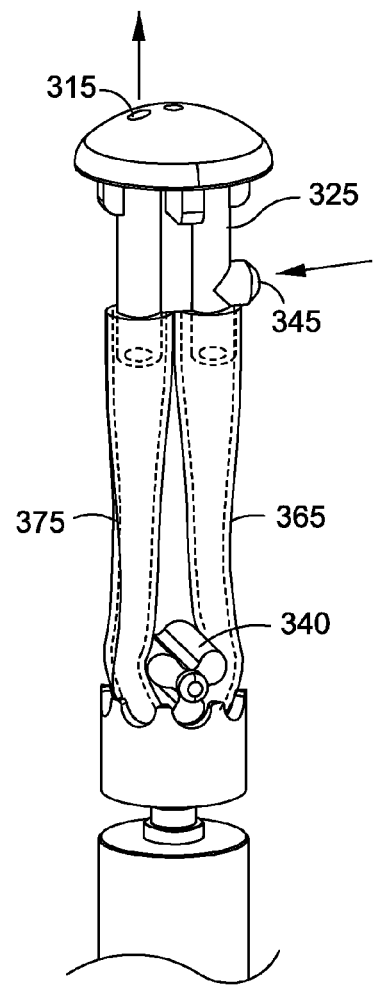
FIG. 5E illustrates a close up view of the peristaltic pump of the balloon device.
Figure 5F:
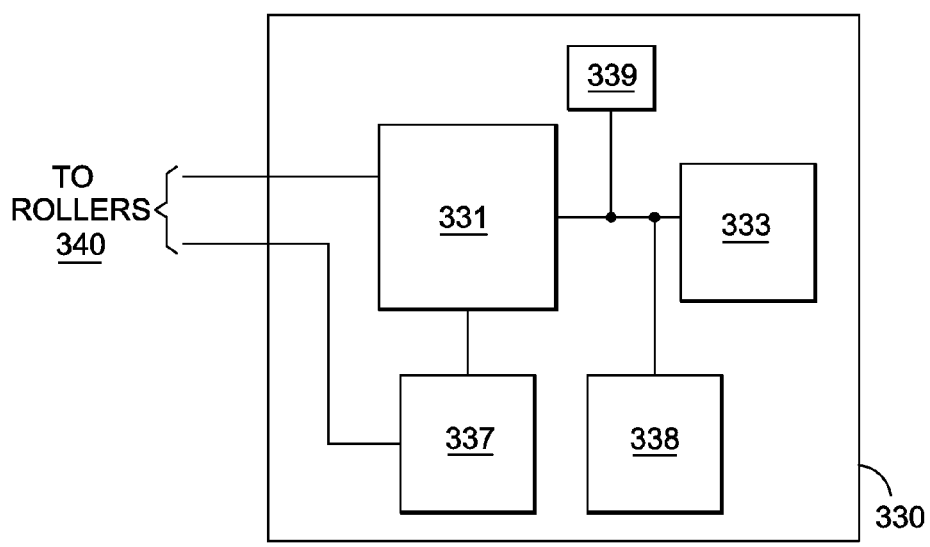
FIG. 5F shows an electronic controller for operating the peristaltic pump of an intragastric balloon device of the three-dimensionally orthogonal intragastric spring device.

As shown in FIG. 5F, the control board 330 may include a processor, physical memory (e.g., a EEPROM, RAM, ROM, etc.), battery and transceiver. The transceiver 338 may allow the control board 330 to communicate with an external computer and receive commands and send status information such as current volume, etc. The control board 330 may further include a sensor 339 configured to detect a current volume of the inflatable balloon device 300. In one embodiment, all the components of the control board 330 may be coupled to one another. In one embodiment, the control board 330 may further include a motor (not shown) to drive the rollers 340. Alternatively, the motor may be part of the roller mechanism 340. Regardless, the processor may drive the rollers 340 to either pump stomach fluid into the inflatable balloon device 300 thereby inflating it to a desirable volume or the processor may drive the rollers 340 to pump stomach fluid out of the inflatable balloon device 300 to deflate it to a desirable volume. More particularly, the processor may control a motor and/or a gearhead, which in turn drives the rollers 340. The memory may store data such as a schedule for inflating or deflating the balloon. In one aspect, the schedule may be updated, changed or interrupted by the transceiver receiving a command from an external computer.

FIG. 5E is a close up view of the peristaltic pump 325 apparatus. As shown, the peristaltic pump 325 includes an external opening 315 leading out through the top of the inflatable balloon device 300, and an internal opening 345 leading out to the side of the tubular body 320 and within the inner cavity of the inflatable layer 305. Rollers 340 of the pump 325 are in contact with flexible tubes 365 and 375 that form a conduit between the external opening 315 and internal opening 345.

In operation, the rollers 340 rotate in a clockwise direction, moving stomach fluid in through the inlet opening 345 as shown and through the distal tube 365 to proximal tube 375 and out external opening 315, thereby deflating the inflatable balloon device 300. To inflate the inflatable balloon device 300, the rollers 340 rotate in a counter-clockwise direction pulling fluid in through external opening 315, down through tube 375, up through tube 365 and out opening 345, in the opposite direction of the arrows. In this fashion the stomach fluid outside the inflatable layer 305 is moved inside the inflatable layer 305, thereby expanding the volume inside the inflatable layer 305.

Figure 5G:
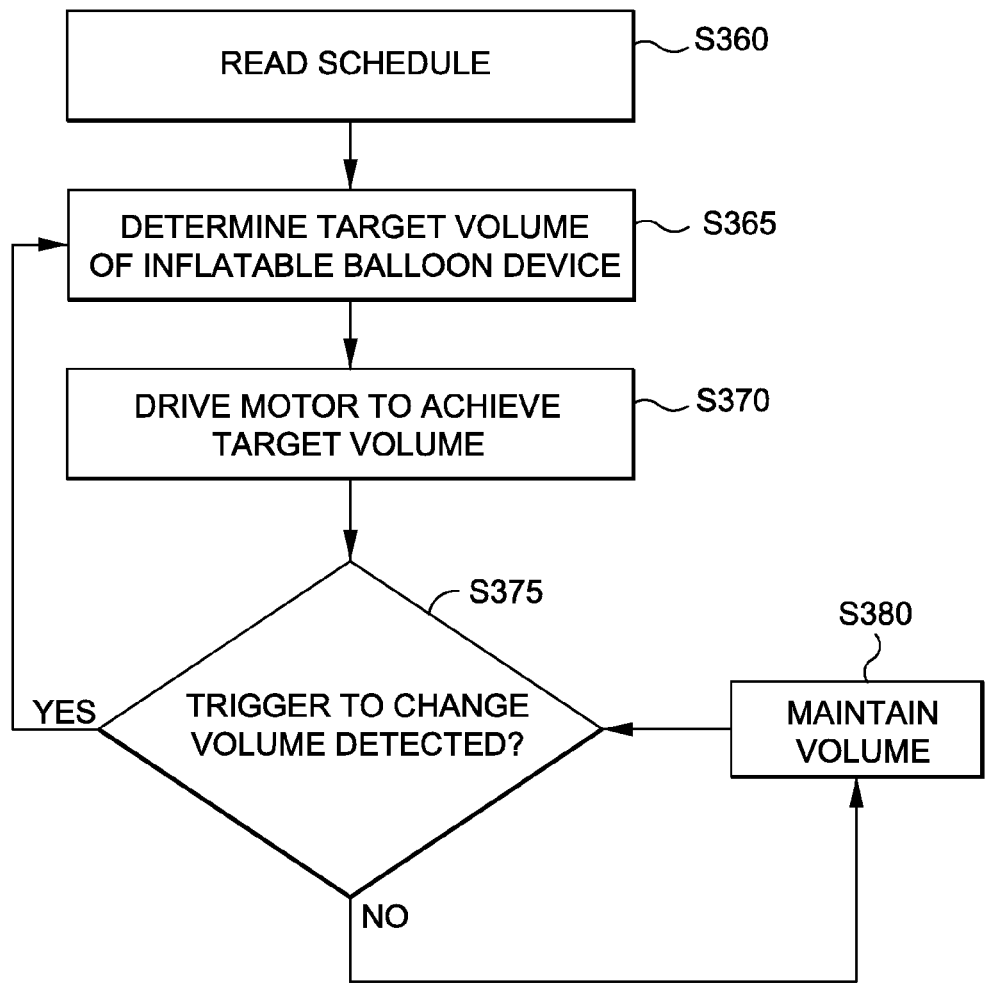
FIG. 5G illustrates a flow chart for controlling the balloon device.

The rollers 340 may be controlled according to any of a number of methods. FIG. 5G illustrates an example of one such method via a flow chart. Initially, when the inflatable balloon device 300 is first deployed in the patient's stomach, inflatable balloon device 300 may read a schedule instructing the different volumes that inflatable balloon device 300 may adjust to and at which times at step S360. In one example, the schedule may be a daily schedule that inflatable balloon device 300 follows. Alternatively, the schedule may be for a week, month, year and so forth. After the schedule is read in step S360, the target volume may be determined according to the schedule at step S365. At step S370, the motor may be driven to achieve the target volume. At step S375, inflatable balloon device 300 may determine if a trigger to change the volume is detected. For example, the trigger may be merely determining that the schedule dictates a changing of the volume of the device 300. Other triggers may include a command from an external computer to change the length of the inflatable balloon device 300.

In one aspect, the external computer may issue a "min volume" command to have inflatable balloon device 300 deflate itself as much as possible. This command may be advantageous, for instance, when the physician is preparing to remove inflatable balloon device 300. The inflatable balloon device 300 may be configured to override the schedule anytime a command is received from the external computer. Referring back to FIG. 5F, in response to the trigger, inflatable balloon device 300 may determine a new target volume and drive the pump to achieve the target volume. However, if at step S375, no trigger is detected, the inflatable balloon device 300 may maintain its current volume until a new trigger is detected to alter the volume.

In one aspect, the volume of the balloon might not decrease beyond a certain predetermined threshold to prevent the inflatable balloon device 300 from getting lodged in the patient's pylorus.

In an alternative embodiment, the top and bottom of the inflatable balloon device 300 may be attached to foldable ends similar to feet 120 of the stomach stimulator as shown in FIGS. 1E, 1F and 1G. In another alternative, the top and bottom of the inflatable balloon device 300 may widen outwards at the two ends, where the diameter of the top and bottom may be sufficiently large enough such that the inflatable balloon device 300 might not be able to fit through the opening of the pylorus.

Accordingly, with or without the foldable feet, the diameter of the tubular body 320 may be 10 mm or less, and the control portion housed within the tubular body may be 8 mm or less in width, and configured to fit inside the tubular body 320.

The insertion process for the inflatable balloon device 300 may be as simple as having the patient swallow the inflatable balloon device 300 while the inflatable balloon device 300 is in a deflated state. Alternatively, the inflatable balloon device 300 in a deflated state may be carefully inserted through the mouth of the patient, down the esophagus and into the patient's stomach by using a standard grabber.

The removal process for the inflatable balloon device 300 may be substantially the reverse of the insertion process. After substantially deflating the inflatable balloon device 300, a standard grabber may be used to clamp onto one end of the inflatable balloon device 300 and pulled back up through the esophagus and out the patient's mouth.

Figure 6:
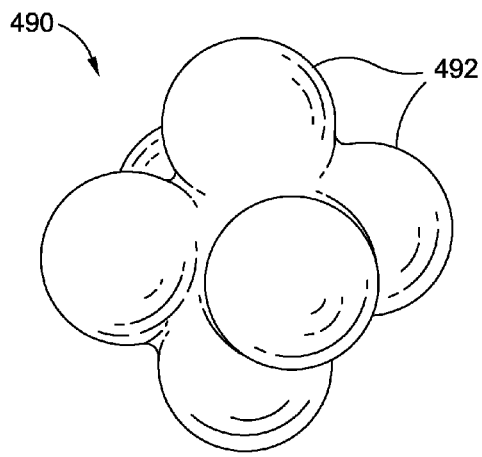
FIGS. 6 and 7 illustrate intragastric devices that encourage rotational variation.
Figure 7:
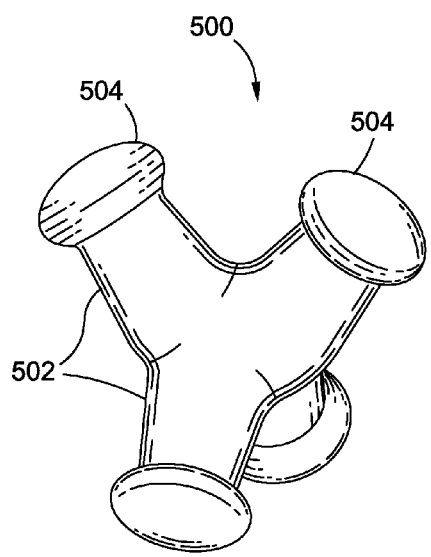

FIGS. 6 and 7 illustrate certain specific features that encourage rotational variation, and may be incorporated into the devices shown herein, in particular to the inflatable balloon device 300 of FIGS. 5A-5G. In FIG. 6, an intragastric obesity treatment device 490 essentially comprises an aggregation of spheres 492. The overall exterior shape of the device is somewhat spherical, encouraging rotation. However, the outwardly projecting spheres that make up the device contact the stomach wall at different locations as the device rotates. In FIG. 7, a device 500 comprises a plurality of outwardly projecting legs 502 terminating in rounded or bulbous feet 504. Again, the device 500 rotates relatively easily within the stomach, especially upon peristaltic motion, and the separated legs 502 and feet 504 therefore contact the stomach wall at different locations on a constantly changing basis. The devices 490, 500 of FIGS. 6 and 7 may also serve to temporarily block the pylorus and slow gastric emptying. These features can be utilized in a device that looks like the device 500, or can be added to a number of the embodiments described herein, such as the inflatable balloon device 300.

Figure 8:
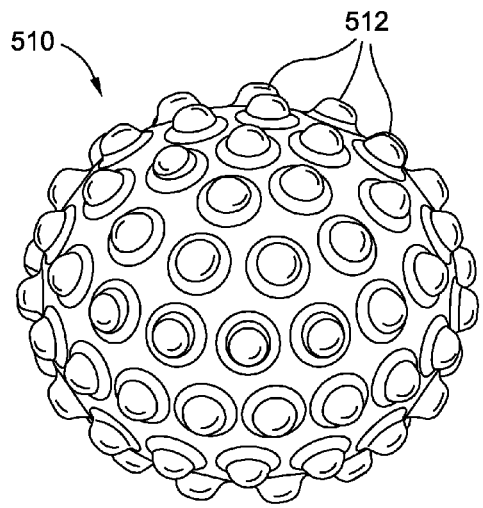
FIGS. 8 and 9 illustrate intragastric devices that both encourage rotational variation and provide additional stomach cavity stimulation.
Figure 9:
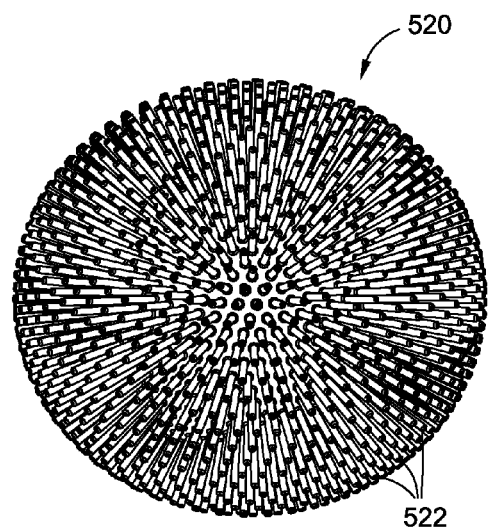

Another option for a number of the intragastric devices disclosed herein is to add uneven external surface stimulation features, such as any raised or depressed geometry which act to stimulate certain portions of the stomach walls. Such features may be particularly effective for those embodiments which stimulate the cardia. For instance, FIG. 8 illustrates a spherical intragastric device 510 having numerous external bumps 512 projecting outward therefrom. These bumps 512 separately contact the inner walls of the stomach, potentially increasing the stimulation to the surrounding satiety-sensing nerves. Another example of exterior stimulation features is seen in FIG. 9, where an intragastric device 520 formed as a sphere features a multitude of small pins or flagella 522 extending outward therefrom. It should be noted that the two embodiments shown in FIGS. 8 and 9 rotate freely within the stomach, such as the inflatable balloon device 300, and that the bumps 512 or flagella 522 may be provided in a non-uniform distribution so as to take advantage of the benefits of the rotational variation described above. That is, a regular array of such exterior features may stimulate the stomach wall more than a smooth surface, but also providing a non-uniform distribution will create different sensations on a constantly changing basis. The bumps 512 or flagella 522 may also be provided on the atraumatic feet 120 of the embodiment in FIGS. 1A-1H or the balloon feet 210, 212 of FIGS. 2-4, to facilitate nerve stimulation.

An alternative intragastric device may include recesses or dimples extending inward from the surface of the intragastric device, much like the reverse of the outward bumps in FIG. 8. For instance, the intragastric device may have a surface comprised of recesses between flat portions. A plurality of such recesses may be equally spaced apart on the outer surface. The recesses may not contact each other, and may be of equal heights and diameters. In addition to being depressed, the recesses may employ a thinner wall. For example, if the flat portions have a wall thickness of 20 millimeters, the recesses may have a wall thickness of 10 millimeters. With a thinner wall, the recesses may be more susceptible to larger strains.

The implantable devices described herein will be subjected to clinical testing in humans. The devices are intended to treat obesity, which is variously defined by different medical authorities. In general, the terms "overweight" and "obese" are labels for ranges of weight that are greater than what is generally considered healthy for a given height. The terms also identify ranges of weight that have been shown to increase the likelihood of certain diseases and other health problems. Applicants propose implanting the devices as described herein into a clinical survey group of obese patients in order to monitor weight loss.

The clinical studies will utilize the devices described above in conjunction with the following parameters.

Materials:
  Silicone materials used include 3206 silicone for any shells, inflatable structures, or otherwise flexible hollow structures. Any fill valves will be made from 4850 silicone with 6% BaSo$_4$. Tubular structures or other flexible conduits will be made from silicone rubber as defined by the Food and Drug Administration (FDA) in the Code of Federal Regulations (CFR) Title 21 Section 177.2600.

Purposes:
  the devices are for human implant,
  the devices are intended to occupy gastric space while also applying intermittent pressure to various and continually changing areas of the stomach;
  the devices are intended to stimulate feelings of satiety, thereby functioning as a treatment for obesity.

General implant procedures:
  The device is intended to be implanted transorally via endoscope into the corpus of the stomach.
  Implantation of the medical devices will occur via endoscopy.
  Nasal/Respiratory administration of oxygen and isoflurane to be used during surgical procedures to maintain anesthesia as necessary.

One exemplary implant procedure is listed below.
a) Perform preliminary endoscopy on the patient to examine the GI tract and determine if there are any anatomical anomalies which may affect the procedure and/or outcome of the study.
b) Insert and introducer into the over-tube.
c) Insert a gastroscope through the introducer inlet until the flexible portion of the gastroscope is fully exited the distal end of the introducer.
d) Leading under endoscopic vision, gently navigate the gastroscope, followed by the introducer/over-tube, into the stomach.
e) Remove gastroscope and introducer while keeping the over-tube in place.
f) OPTIONAL: Place the insufflation cap on the over-tubes inlet, insert the gastroscope, and navigate back to the stomach cavity.
g) OPTIONAL: Insufflate the stomach with air/inert gas to provide greater endoscopic visual working volume.
h) Collapse the gastric implant and insert the lubricated implant into the over-tube, with inflation catheter following if required.
i) Under endoscopic vision, push the gastric implant down the over-tube with gastroscope until visual confirmation of deployment of the device into the stomach can be determined.
j) Remove the guide-wire from the inflation catheter is used.
k) If inflated: Inflate the implant using a standard BioEnterics Intragastric Balloon System ("BIB System") Fill kit.
l) Using 50-60 cc increments, inflate the volume to the desired fill volume.
m) Remove the inflation catheter via over-tube.
n) Inspect the gastric implant under endoscopic vision for valve leakage, and any other potential anomalies. Record all observations.
o) Remove the gastroscope from over-tube.
p) Remove the over-tube from the patient.

End Point Criteria:
Weight Loss
Comprehensive Metabolic Panel (CMP)
HbAlC
Lipid Panel
Tissue Samples/Response Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention(especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, references may have been made to patents and printed publications in this specification. Each of the above-cited references and printed publications are individually incorporated herein by reference in their entirety.

Specific embodiments disclosed herein may be further limited in the claims using "consisting of" or "consisting essentially of" language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A system for an implantable device, the device being of a size that is too large to pass through an opening of a patient's pylorus, the device constructed for placement completely within a patient's stomach and constructed to be introduced into the stomach transorally without surgery to treat and prevent obesity by applying an outwardly directed pressure to the patient's stomach from within the stomach, comprising:

a central elongated body having telescopically adjustable length and a longitudinal axis;

two collapsible atraumatic feet extending from opposite ends of the elongated body, each foot constructed to assume an elongated delivery configuration in which the foot is positioned at a first radially collapsed position where said feet are elongated along said longitudinal axis, and to move to a deployed configuration in which the foot is in a second radially expanded position where said feet form stomach-contacting surfaces that are substantially perpendicular to said longitudinal axis at opposite ends of the elongated body, the two collapsible atraumatic feet comprising an array of living hinges that may be unfolded to said elongated delivery configuration and folded outward to said deployed configuration, each foot configured to exert an outwardly directed pressure on an interior of the patient's stomach from within the stomach when the foot is in the deployed configuration when the central elongated body and the atraumatic feet are completely contained within the interior of the stomach without the elongated body piercing any portion of the stomach, wherein the central elongated body does not pass through the atraumatic feet along the longitudinal axis; and an actuator at least partially within the central elongated body configured to simultaneously adjust the length of the body and the distance between the atraumatic feet.

2. The system of claim 1, wherein the two collapsible atraumatic feet comprise balloon-like structures.

3. The system of claim 1, wherein the array of living hinges are in an X-shape.

4. A system for an implantable device, the device being of a size that is too large to pass through an opening of a patient's pylorus, the device constructed for deployment completely within a patient's stomach and constructed to be introduced into the stomach transorally without surgery to treat and prevent obesity by applying an outwardly directed pressure to the patient's stomach from within the stomach, comprising:

a central elongated body having an adjustable length;

two collapsible atraumatic feet on opposite ends of the elongated body, each foot constructed to exert an outwardly directed pressure on an interior of the patient's stomach from within the stomach when the foot is in a deployed configuration when the central elongated body and the two atraumatic feet are completely contained within the interior of the stomach without the elongated body piercing any portion of the stomach; and an actuator comprising an electronic motor within the central elongated body, the electric motor actuated to simultaneously adjust the length of the body and the distance between the atraumatic feet.

5. The system of claim 4, wherein the actuator further comprises a control circuit board having a battery and a memory.

6. The system of claim 5, wherein the actuator further comprises a control circuit board having a transceiver, and the system further includes a remote control for instructing the motor from outside the patient's body.

7. The system of claim 4, wherein the actuator further comprises a telescoping screw driven by the motor.

8. A system for an implantable device, the device being of a size that is too large to pass through an opening of a patient's pylorus, the device constructed for placement completely within a patient's stomach and constructed to be introduced into the stomach transorally without surgery to treat and prevent obesity by applying an outwardly directed pressure to the patient's stomach from within the stomach, comprising:
a central elongated body having telescopically adjustable length and a longitudinal axis;
two collapsible atraumatic feet extending from opposite ends of the elongated body, each foot constructed to assume an elongated delivery configuration in which the foot is positioned at a first radially collapsed position where said feet are elongated along said longitudinal axis, and to move to a deployed configuration in which the foot is in a second radially expanded position where said feet form stomach-contacting surfaces that are substantially perpendicular to said longitudinal axis at opposite ends of the elongated body, each foot configured to exert an outwardly directed pressure on an interior of the patient's stomach from within the stomach when the foot is in the deployed configuration when the central elongated body and the atraumatic feet are completely contained within the interior of the stomach without the elongated body piercing any portion of the stomach, wherein the central elongated body does not pass through the atraumatic feet along the longitudinal axis; and
an actuator at least partially within the central elongated body configured to simultaneously adjust the length of the body and the distance between the atraumatic feet, wherein the actuator comprises an acid-activated lengthening polymer element that is acid-activated to lengthen in a highly acidic environment, and the central elongated body defines through holes for exposing the polymer element to the stomach environment.

9. The system of claim 8, wherein the central elongated body comprises a series of telescoping tubular members having apertures along their lengths.

10. The system of claim 1, wherein the atraumatic feet include uneven external surface stimulation features.

11. The system of claim 1, wherein the actuator is contained within the central elongated body.

12. The system of claim 11, wherein the actuator is configured such that when the actuator is actuated the length of the body and the distance between the atraumatic feet are simultaneously adjusted.

13. The system of claim 11, wherein the actuator is configured such that when the actuator is actuated the length of the body and the radially expanded position of at least one of the atraumatic feet are simultaneously adjusted.

14. A system for an implantable device, the device being of a size that is too large to pass through an opening of a patient's pylorus, the device constructed for placement completely within a patient's stomach and constructed to be introduced into the stomach transorally without surgery to treat and prevent obesity by applying an outwardly directed pressure to the patient's stomach from within the stomach, comprising:
a central elongated body having telescopically adjustable length and a longitudinal axis;
two collapsible atraumatic feet on opposite ends of the elongated body, each foot constructed to assume an elongated delivery configuration in which the foot is positioned at a first radially collapsed position where said feet are elongated along said longitudinal axis, and to move to a deployed configuration in which the foot is in a second radially expanded position where said feet form stomach-contacting surfaces that are substantially perpendicular to said longitudinal axis at opposite ends of the elongated body, each foot configured to exert an outwardly directed pressure on an interior of the patient's stomach from within the stomach when the foot is in the deployed configuration when the central elongated body and the atraumatic feet are completely contained within the interior of the stomach without the elongated body piercing any portion of the stomach; and
an actuator within the central elongated body configured to simultaneously adjust the length of the body and the distance between the atraumatic feet,
wherein the actuator includes a piston that biases the atraumatic feet away from each other.

15. A system for an implantable device, the device being of a size that is too large to pass through an opening of a patient's pylorus, the device constructed for placement completely within a patient's stomach and constructed to be introduced into the stomach transorally without surgery to treat and prevent obesity by applying an outwardly directed pressure to the patient's stomach from within the stomach, comprising:
a central elongated body having telescopically adjustable length and a longitudinal axis;
two collapsible atraumatic feet extending from opposite ends of the elongated body, each foot constructed to assume an elongated delivery configuration in which the foot is positioned at a first radially collapsed position where said feet are elongated along said longitudinal axis, and to move to a deployed configuration in which the foot is in a second radially expanded position where said feet form stomach-contacting surfaces that are substantially perpendicular to said longitudinal axis at opposite ends of the elongated body, each foot configured to exert an outwardly directed pressure on an interior of the patient's stomach from within the stomach when the foot is in the deployed configuration when the central elongated body and the atraumatic feet are completely contained within the interior of the stomach without the elongated body piercing any portion of the stomach, wherein the central elongated body does not pass through the atraumatic feet along the longitudinal axis; and
an actuator at least partially within the central elongated body configured to simultaneously adjust the length of the body and the distance between the atraumatic feet, the actuator including a telescoping screw to operably shorten or lengthen the central elongated body.

16. The system of claim 1, wherein the actuator is configured to adjust the length of the body and the distance between the atraumatic feet at random or pre-set distances and at random or pre-set time intervals.

17. The system of claim 1, wherein at least one of the atraumatic feet is comprised of an array of discrete collapsible fingers.

18. The system of claim 17, wherein each finger is formed as a loop that extends in a plane and wherein each finger is configured to bend about thinned regions of each loop such that the finger is collapsible within its respective plane.

19. The system of claim 18, wherein the plane is parallel to the longitudinal axis.

20. The system of claim 18, wherein each loop has a first end and a second end opposite the first end, wherein the first ends of all of the loops of one foot are joined to an end of the elongated body and the second ends of all of the loops, opposite the first ends, are joined together at a location longitudinally spaced from the end of the elongated body.

21. The system of claim 17, wherein in the deployed configuration the fingers extend radially with respect to the longitudinal axis.

\* \* \* \* \*